(12) United States Patent
Kung et al.

(10) Patent No.: US 7,297,820 B2
(45) Date of Patent: Nov. 20, 2007

(54) STILBENE DERIVATIVES AND THEIR USE FOR BINDING AND IMAGING AMYLOID PLAQUES

(75) Inventors: Hank F. Kung, Wynnewood, PA (US); Mei-Ping Kung, Wynnewood, PA (US); Zhi-Ping Zhuang, Lansdale, PA (US)

(73) Assignee: Trustees of The University of Pennsylvania, Philadelphia, PA (US)

( * ) Notice: Subject to any disclaimer, the term of this patent is extended or adjusted under 35 U.S.C. 154(b) by 0 days.

(21) Appl. No.: 11/218,587

(22) Filed: Sep. 6, 2005

(65) Prior Publication Data
US 2006/0002853 A1 Jan. 5, 2006

Related U.S. Application Data

(62) Division of application No. 10/228,275, filed on Aug. 27, 2002.

(60) Provisional application No. 60/314,658, filed on Aug. 27, 2001.

(51) Int. Cl.
*C07C 211/00* (2006.01)
*A61K 31/135* (2006.01)

(52) U.S. Cl. ............... 564/336; 564/340; 564/440; 514/646; 514/649

(58) Field of Classification Search ........... 564/336, 564/340, 440; 514/646, 649
See application file for complete search history.

(56) References Cited

U.S. PATENT DOCUMENTS

| 4,001,229 | A | * | 1/1977 | Kreighbaum | ............... 544/159 |
| 5,525,632 | A | | 6/1996 | Obsumi et al. | |
| 5,601,801 | A | | 2/1997 | Flanagan et al. | |
| 2003/0149250 | A1 | | 8/2003 | Kung et al. | |

OTHER PUBLICATIONS

Attiná, M., et al., "Labeled Aryl Fluorides from the Nucleophilic Displacement of Activated Nitro Groups by $^{18}$F-F," *J. Labelled Comp. Radiopharm.* XX:501-514, John Wiley & Sons, Ltd. (1983).
Counsell, R.E., et al., "Radioiodinated Estrogens and Antiestrogens as Potential Imaging Agents," *Curr. Top. Mol. Endocrinol.* 4:107-113, Plenum Press (1976).
Diana, G.D., et al., "Antiviral Activity of Some β-Diketones. 4. Benzyl Diketones. In Vitro Activity against Both RNA and DNA Viruses," *J. Med. Chem.* 21:889-894, American Chemical Society (1978).
Gascoyne, J.M., et al., "Fluorine-19 Nuclear Magnetic Resonance Studies of Aromatic Compounds. Part 5. Transmission of Substituent Effects across Two Aromatic Rings connected by C—C and —C—Linkages," *J. Chem. Soc. Perkin Trans. II*:1051-1057, The Chemical Society (1977).
Klunk, W.E., et al., "Staining of AD and Tg2576 Mouse Brain with X-34, a Highly Fluorescent Derivative of Chrysamine G and a Potential In Vivo Probe for β-sheet Fibrils," *Abstr. Soc. Neurosci.* 23:1638, Abstract No. 636.12, Society for Neuroscience (1997).
Kruijer, P.S., et al., "Biodistribution of $^{123}$I-Labeled 4-Hydroxytamoxifen Derivatives in Rats with Dimethylbenzanthracene-Induced Mammary Carcinomas," *Nucl. Med. Biol.* 24:719-722, Elsevier Science Inc. (1997).
Kumari, N., et al., "Studies on Ylides Exclusive Formation of Olefins From Carbonyl Compounds on Treatment with *para*-Bromo- and *para*-Iodo-Benzylidenetriphenylarsenanes," *J. Organomet. Chem.* 96:237-241, Elsevier Sequoia S.A., Lausanne (1975).
Kung, H.F., et al., "Novel Stilbenes as Probes for Amyloid Plaques," *J. Am. Chem. Soc.* 123:12740-12741, American Chemical Society (available online Nov. 2001).
Ho, T.-I., et al., "Novel Photochemical Rearrangement of Styrylfurans," *Angew. Chem. Int. Ed. Engl.* 38:2558-2560, Verlag Chemie (1999).
Holand, S., et al., "Acetylenic glycols. VI. Relation between the structure and the cyclization ability in alkaline medium," *Chemical Abstracts 78*, American Chemical Society, Abstract No. 71798 (1973).
Supplementary Partial European Search Report for European Patent Application No. EP 02757398.9, European Patent Office, Netherlands, mailed Dec. 29, 2006.
Ager, I.R. and Phillips, L., "$^{19}$F Nuclear Magnetic Resonance Studies of Aromatic Compounds. Part I. The Effect of Solvents on the Chemical Shift of Fluorine Nuclei in *para*-Substituted Fluorobenzenes, 4-Substituted 4'-Fluoro-*trans*-stilbenes, and 4-Substituted 3'-Fluoro-*trans*-stilbenes," *J.C.S. Perkin II*, 1975-1982, 1993, Journal of the Chemical Society (1972).
Annunziata, R. and Colonna, S., "Stereochemistry of α-Halogeno-sulphoxides. Part 5. Absolute Stereochemistry of α-Chlorination of Benzyl t-Butyl Sulphoxide," *J.C.S. Perkin I*, 1052-1056, Journal of the Chemical Society (1977).
Arbez-Gindre, C. et al., "Organolithium reagents bearing nonlinear optical chromophores. Synthesis of triarylmethane dyes," *Tetrahedron Lett.* 40:7413-7416, Elsevier Science Ltd. (1999).
Ashburn, T.T. et al., "Amyloid probes based on Congo Red distinguish between fibrils comprising different peptides," *Chem. Biol.* 3:351-358, Current Biology Ltd. (1996).
Berge, S.M. et al., "Pharmaceutical Salts," *J. Pharm. Sci.* 66:1-19, American Pharmaceutical Association (1977).
Database CAPLUS on STN, Chemical abstracts, Accession No. 1976:73777, Tewari, R.S. et al., "Generation and reactions of some dimethyl benzylphosphonate carbanions: synthesis of trans-diaryl-substituted ethylenes," *J. Chem. Eng. Data 21* (I):125-131 (1976), abstract.
Diana, G.D. et al., "Antiviral Activity of Some β-Diketones. 4. Benzyl Diketones. In Vitro Activity against both RNA and DNA Viruses," *J. Med. Chem.* 21:889-891, American Chemical Society (1978).

(Continued)

Primary Examiner—Shailendra Kumar
(74) Attorney, Agent, or Firm—Woodcock Washburn LLP

(57) ABSTRACT

This invention relates to a method of imaging amyloid deposits and to labeled compounds, and methods of making labeled compounds useful in imaging amyloid deposits. This invention also relates to compounds, and methods of making compounds for inhibiting the aggregation of amyloid proteins to form amyloid deposits, and a method of delivering a therapeutic agent to amyloid deposits.

10 Claims, 5 Drawing Sheets

OTHER PUBLICATIONS

Elhaddaoui, A. et al., "Competition of Congo Red and Thioflavin S Binding to Amyloid Sites in Alzheimer's Diseased Tissue," *Biospectroscopy* 1:351-356, John Wiley & Sons Inc. (1995).

Findeis, M.A., "Approaches to discovery and characterization of inhibitors of amyloid β-peptide polymerization," *Biochim. Biophys. Acta* 1502:76-84, Elsevier Science B.V. (Jul. 2000).

Ginsberg, S.D. et al., "Molecular Pathology of Alzheimer's Disease and Related Disorders," in *Cereb. Cortex*, Peters, A., and Morrison, J.H., eds., Kluwer Academic/Plenum Publishers, New York, NY, pp. 603-654 (1999).

Golde, T.E. et al., "Biochemical detection of Aβ isoforms: implications for pathogenesis, diagnosis, and treatment of Alzheimer's disease," *Biochim. Biophys. Acta* 1502:172-187, Elsevier Science B.V. (Jul. 2000).

Han, H. et al., "Technetium Complexes for the Quantitation of Brain Amyloid," *J. Am. Chem. Soc.* 118:4506-4507, American Chemical Society (1996).

International Search Report for International Application No. PCT/US02/27201 mailed on Dec. 20, 2002.

Klunk, W.E. et al., "Quantitative Evaluation of Congo Red Binding to Amyloid-like Proteins with a Beta-pleated Sheet Conformation," *J. Histochem. Cytochem.* 37:1273-1281, The Histochemical Society, Inc. (1989).

Klunk, W.E. et al., "Quantitative in vitro NMR analysis of Alzheimer's, non-Alzheimer's demented and Control Brain," *Biol. Psychiatry* (Abstracts)35:627, Abstract No. 44., Elsevier (1994).

Klunk, W.E. et al., "Chrysamine-G Binding to Alzheimer and Control Brain: Autopsy Study of a New Amyloid Probe," *Neurobiol. Aging* 16:541-548, Elsevier Science Ltd. (1995).

Klunk, W.E. et al., "Staining of AD and Tg2576 mouse brain with X-34, a highly fluorescent derivative of chrysamine G and a potential in vivo probe for β-sheet fibrils," *Abstr. Soc. Neurosci.* 23:1638, Abstract No. 636.12, Society for Neuroscience (1997).

Kumari, N. et al., "Studies on Ylides Exclusive Formation of Olefins From Carbonyl Compounds on Treatment with *para*-Bromo- and *para*-Iodo-Benzylidenetriphenylarsenanes," *J. Org. Chem.* 96:237-241, Elsevier Sequoia S.A., Lausanne, The Netherlands (1975).

Kuner, P. et al., "Controlling Polymerization of β-Amyloid and Prion-derived Peptides with Synthetic Small Molecule Ligands," *J. Biol. Chem.* 275:1673-1678, The American Society for Biochemistry and Molecular Biology, Inc. (Jan. 2000).

Lee, C-W. et al., "Isomerization of (Z,Z) to (E,E)1-Bromo-2,5-bis-(3-hydroxycarbonyl-4-hydroxy)-styrylbenzene in Strong Base: Probes for Amyloid Plaques in the Brain," *J. Med. Chem.* 44:2270-2275, American Chemical Society (Jul. 2001).

Lorenzo, A., and Yankner, B.A., "β-Amyloid neurotoxicity requires fibril formation and is inhibited by Congo red," *Proc. Natl. Acad. Sci. USA* 91:12243-12247, National Academy Press (1994).

Mathis, C.A. et al., "Synthesis of a Lipophilic, Radioiodinated Ligand with High Affinity to Amyloid Protein in Alzheimer's Disease Brain Tissue," *J. Labelled Cpd. Radiopharm.* 40:94-95, John Wiley & Sons, Ltd. (1997).

Moore, C.L. et al., "Difluoro Ketone Peptidomimetics Suggest a Large S1 Pocket for Alzheimer's γ-Secretase: Implications for Inhibitor Design," *J. Med. Chem.* 43:3434-3442, American Chemical Society (Sep. 2000).

Näslund, J. et al., "Correlation Between Elevated Levels of Amyloid β-Peptide in the Brain and Cognitive Decline," *JAMA* 283:1571-1577, American Medical Association (Mar. 2000).

Selkoe, D.J. "Biology of β-Amyloid Precursor Protein and the Mechanism of Alzheimer Disease," in *Alzheimer Disease*, 2nd edition, Terry, R.D. et al., eds., Lippincott Williams & Wilkins, Philadelphia, PA, pp. 293-310 (1999).

Selkoe, D.J., "The Origins of Alzheimer Disease. A is for Amyloid," *JAMA* 283:1615-1617, American Medical Association (Mar. 2000).

Skovronsky, D.M., and Lee, V. M. Y., "β-Secretase revealed: starting gate for race to novel therapies for Alzheimer's disease," *Trends Pharmacol. Sci.* 21:161-163, Elsevier (May 2000).

Vassar, R. et al., "β-Secretase Cleavage of Alzheimer's Amyloid Precursor Protein by the Transmembrane Aspartic Protease BACE," *Science* 286:735-741, American Association for the Advancement of Science (1999).

Vogelsberg-Ragaglia, V. et al., "Cell Biology of Tau and Cytoskeletal Pathology in Alzheimer Disease," in *Alzheimer Disease*, 2nd edition, Terry, R.D. et al., eds., Lippincott Williams & Wilkins, Philadelphia, PA, pp. 359-372 (1999).

Wolfe, M.S. et al., "A Substrate-Based Difluoro Ketone Selectively Inhibits Alzheimer's γ-Secretase Activity," *J. Med. Chem.* 41:6-9, American Chemical Society (1998).

Xia, W. et al., "Presenilin complexes with the C-terminal fragments of amyloid precursor protein at the sites of amyloid β-protein generation," *Proc. Natl. Acad. Sci. USA* 97:9299-9304, National Academy Press (Aug. 2000).

Zhen, W. et al., "Synthesis and Amyloid Binding Properties of Rhenium Complexes: Preliminary Progress Toward a Reagent for SPECT Imaging of Alzheimer's Disease Brain," *J. Med. Chem.* 42:2805-2815, American Chemical Society (1999).

Zhuang, Z.-P. et al., "Radioiodinated Styrylbenzenes and Thioflavins as Probes for Amyloid Aggregates," *J. Med. Chem.* 44:1905-1914, American Chemical Society (Jun. 2001).

Co-pending U.S. Appl. No. 11/305,333, inventors: Kung, H.F. et al., filed Dec. 19, 2005 (Not Published).

Co-pending U.S. Appl. No. 11/305,350, inventors: Kung, H.F. et al., filed Dec. 19, 2005 (Not Published).

\* cited by examiner

STILBENE DERIVATIVES AND THEIR USE FOR BINDING AND IMAGING AMYLOID PLAQUES

CROSS REFERENCE TO RELATED APPLICATIONS

This application is a divisional of U.S. application Ser. No. 10/228,275, filed on Aug. 27, 2002, which claims the benefit of Provisional Application No. 60/314,658, filed Aug. 27, 2001, the contents of which are fully incorporated by reference herein.

STATEMENT REGARDING FEDERALLY-SPONSORED RESEARCH AND DEVELOPMENT

Part of the work performed during development of this invention utilized U.S. Government funds. The U.S. Government has certain rights in this invention under grant numbers NS-18509 and PO1 AG-11542 awarded by the Institute for the Study of Aging.

BACKGROUND OF THE INVENTION

1. Field of the Invention

This invention relates to novel bioactive compounds, methods of diagnostic imaging using radiolabeled compounds, and methods of making radiolabeled compounds.

2. Background Art

Alzheimer's disease (AD) is a progressive neurodegenerative disorder characterized by cognitive decline, irreversible memory loss, disorientation, and language impairment. Postmortem examination of AD brain sections reveals abundant senile plaques (SPs) composed of amyloid-β (Aβ) peptides and numerous neurofibrillary tangles (NFTs) formed by filaments of highly phosphorylated tau proteins (for recent reviews and additional citations see Ginsberg, S. D., et al., "Molecular Pathology of Alzheimer's Disease and Related Disorders," in *Cerebral Cortex: Neurodegenerative and Age-related Changes in Structure and Function of Cerebral Cortex*, Kluwer Academic/Plenum, NY (1999), pp. 603-654; Vogelsberg-Ragaglia, V., et al., "Cell Biology of Tau and Cytoskeletal Pathology in Alzheimer's Disease," *Alzheimer's Disease*, Lippincot, Williams & Wilkins, Philadelphia, Pa. (1999), pp. 359-372). Familial AD (FAD) is caused by multiple mutations in the A precursor protein (APP), presenilin 1 (PS1) and presenilin 2 (PS2) genes (Ginsberg, S. D., et al., "Molecular Pathology of Alzheimer's Disease and Related Disorders," in *Cerebral Cortex: Neurodegenerative and Age-related Changes in Structure and Function of Cerebral Cortex*, Kluwer Academic/Plenum, NY (1999), pp. 603-654; Vogelsberg-Ragaglia, V., et al., "Cell Biology of Tau and Cytoskeletal Pathology in Alzheimer's Disease," *Alzheimer's Disease*, Lippincot, Williams & Wilkins, Philadelphia, Pa. (1999), pp. 359-372).

While the exact mechanisms underlying AD are not fully understood, all pathogenic FAD mutations studied thus far increase production of the more amyloidogenic 42-43 amino-acid long form of the Aβ peptide. Thus, at least in FAD, dysregulation of Aβ production appears to be sufficient to induce a cascade of events leading to neurodegeneration. Indeed, the amyloid cascade hypothesis suggests that formation of extracellular fibrillar Aβ aggregates in the brain may be a pivotal event in AD pathogenesis (Selkoe, D. J., "Biology of B-amyloid Precursor Protein and the Mechanism of Alzheimer's Disease," *Alzheimer's Disease*, Lippincot Williams & Wilkins, Philadelphia, Pa. (1999), pp. 293-310; Selkoe, D. J., *J. Am. Med. Assoc.* 283:1615-1617 (2000); Naslund, J., et al., *J. Am. Med. Assoc.* 283:1571-1577 (2000); Golde, T. E., et al., *Biochimica et Biophysica Acta* 1502:172-187 (2000)).

Various approaches in trying to inhibit the production and reduce the accumulation of fibrillar Aβ in the brain are currently being evaluated as potential therapies for AD (Skovronsky, D. M. and Lee, V. M., *Trends Pharmacol. Sci.* 21:161-163 (2000); Vassar, R., et al., *Science* 286:735-741 (1999); Wolfe, M. S., et al., *J. Med. Chem.* 41:6-9 (1998); Moore, C. L., et al., *J. Med. Chem.* 43:3434-3442 (2000); Findeis, M. A., *Biochimica et Biophysica Acta* 1502:76-84 (2000); Kuner, P., Bohrmann, et al., *J. Biol. Chem.* 275: 1673-1678 (2000)). It is therefore of great interest to develop ligands that specifically bind fibrillar Aβ aggregates. Since extracellular SPs are accessible targets, these new ligands could be used as in vivo diagnostic tools and as probes to visualize the progressive deposition of Aβ in studies of AD amyloidogenesis in living patients.

To this end, several interesting approaches for developing fibrillar Aβ aggregate-specific ligands have been reported (Ashburn, T. T., et al., *Chem. Biol.* 3:351-358 (1996); Han, G., et al., *J. Am. Chem. Soc.* 118:4506-4507 (1996); Klunk, W. E., et al., *Biol. Psychiatry* 35:627 (1994); Klunk, W. E., et al., *Neurobiol. Aging* 16:541-548 (1995); Klunk, W. E., et al., *Society for Neuroscience Abstract* 23:1638 (1997); Mathis, C. A., et al., *Proc. XIIth Intl. Symp. Radiopharm. Chem.*, Uppsala, Sweden: 94-95 (1997); Lorenzo, A. and Yankner, B. A., *Proc. Natl. Acad. Sci. U.S.A.* 91:12243-12247 (1994); Zhen, W., et al., *J. Med. Chem.* 42:2805-2815 (1999)). The most attractive approach is based on highly conjugated chrysamine-G (CG) and Congo red (CR), and the latter has been used for fluorescent staining of SPs and NFTs in postmortem AD brain sections (Ashburn, T. T., et al., *Chem. Biol.* 3:351-358 (1996); Klunk, W. E., et al., *J. Histochem. Cytochem.* 37:1273-1281 (1989)). The inhibition constants ($K_i$) for binding to fibrillar Aβ aggregates of CR, CG, and 3'-bromo- and 3'-iodo derivatives of CG are 2,800, 370, 300 and 250 nM, respectively (Mathis, C. A., et al., *Proc. XIIth Intl. Symp. Radiopharm. Chem.*, Uppsala, Sweden: 94-95 (1997)). These compounds have been shown to bind selectively to Aβ (1-40) peptide aggregates in vitro as well as to fibrillar Aβ deposits in AD brain sections (Mathis, C. A., et al., *Proc. XIIth Intl. Symp. Radiopharm. Chem.*, Uppsala, Sweden: 94-95 (1997)).

Amyloidosis is a condition characterized by the accumulation of various insoluble, fibrillar proteins in the tissues of a patient. An amyloid deposit is formed by the aggregation of amyloid proteins, followed by the further combination of aggregates and/or amyloid proteins. Formation and accumulation of aggregates of β-amyloid (Aβ) peptides in the brain are critical factors in the development and progression of AD. The fibrillar aggregates of amyloid peptides, $A\beta_{1-40}$ and $A\beta_{1-42}$, are major metabolic peptides derived from amyloid precursor protein found in senile plaques and cerebrovascular amyloid deposits in AD patients (Xia, W., et al., *J. Proc. Natl. Acad. Sci. U.S.A.* 97:9299-9304 (2000)). Prevention and reversal of Aβ plaque formation are being targeted as a treatment for this disease (Selkoe, D., J. JAMA 283:1615-1617 (2000); Wolfe, M. S., et al., *J. Med. Chem.* 41:6-9 (1998); Skovronsky, D. M., and Lee, V. M., *Trends Pharmacol. Sci.* 21:161-163 (2000)).

In addition to the role of amyloid deposits in Alzheimer's disease, the presence of amyloid deposits has been shown in diseases such as Mediterranean fever, Muckle-Wells syndrome, idiopathic myeloma, amyloid polyneuropathy, amyloid cardiomyopathy, systemic senile amyloidosis, amyloid polyneuropathy, hereditary cerebral hemorrhage with amyloidosis, Down's syndrome, Scrapie, Creutzfeldt-Jacob disease, Kuru, Gerstamnn-Straussler-Scheinker syndrome, medullary carcinoma of the thyroid, Isolated atrial amyloid, $\beta_2$-microglobulin amyloid in dialysis patients, inclusion body myositis, $\beta_2$-amyloid deposits in muscle wasting disease, and Islets of Langerhans diabetes Type II insulinoma.

Thus, a simple, noninvasive method for detecting and quantitating amyloid deposits in a patient has been eagerly sought. Presently, detection of amyloid deposits involves histological analysis of biopsy or autopsy materials. Both methods have drawbacks. For example, an autopsy can only be used for a postmortem diagnosis.

Imaging agents may be based on two types of isotopes. $^{99m}$Tc ($T_{1/2}$, 6 h; 140 KeV) and $^{123}$I ($T_{1/2}$, 13 h; 159 KeV) are routinely used for single photon emission computed tomography (SPECT), while $^{11}$C ($T_{1/2}$, 20 min; 511 KeV) and $^{18}$F ($T_{1/2}$, 110 min; 511 KeV) are commonly used for positron emission tomography (PET).

The direct imaging of amyloid deposits in vivo is difficult, as the deposits have many of the same physical properties (e.g., density and water content) as normal tissues. Attempts to image amyloid deposits using magnetic resonance imaging (MRI) and computer-assisted tomography (CAT) have been disappointing and have detected amyloid deposits only under certain favorable conditions. In addition, efforts to label amyloid deposits with antibodies, serum amyloid P protein, or other probe molecules have provided some selectivity on the periphery of tissues, but have provided for poor imaging of tissue interiors.

Potential ligands for detecting Aβ aggregates in the living brain must cross the intact blood-brain barrier. Thus brain uptake can be improved by using ligands with relatively smaller molecular size (compared to Congo Red) and increased lipophilicity. Highly conjugated thioflavins (S and T) are commonly used as dyes for staining the Aβ aggregates in the AD brain (Elhaddaoui, A., et al., *Biospectroscopy* 1: 351-356 (1995)). These compounds are based on benzothiazole, which is relatively small in molecular size.

It would be useful to have a noninvasive technique for imaging and quantitating amyloid deposits in a patient. In addition, it would be useful to have compounds that inhibit the aggregation of amyloid proteins to form amyloid deposits and a method for determining a compound's ability to inhibit amyloid protein aggregation.

SUMMARY OF THE INVENTION

The present invention provides novel compounds of Formula I, II, III IV or V.

The present invention also provides diagnostic compositions comprising a radiolabeled compound of Formula I, II, III, IV or V and a pharmaceutically acceptable carrier or diluent.

The invention further provides a method of imaging amyloid depositis, the method comprising introducing into a patient a detectable quantity of a labeled compound of Formula I, II, III, IV or V or a pharmaceutically acceptable salt, ester, amide or prodrug thereof.

The present invention also provides a method for inhibiting the aggregation of amyloid proteins, the method comprising administering to a mammal an amyloid inhibiting amount of a compound Formula I, II, III, IV or V or a pharmaceutically acceptable salt, ester, amide, or prodrug thereof.

A further aspect of this invention is directed to methods and intermediates useful for synthesizing the amyloid inhibiting and imaging compounds of Formula I, II, III, IV or V described herein.

DETAILED DESCRIPTION OF THE INVENTION

Figure 1:
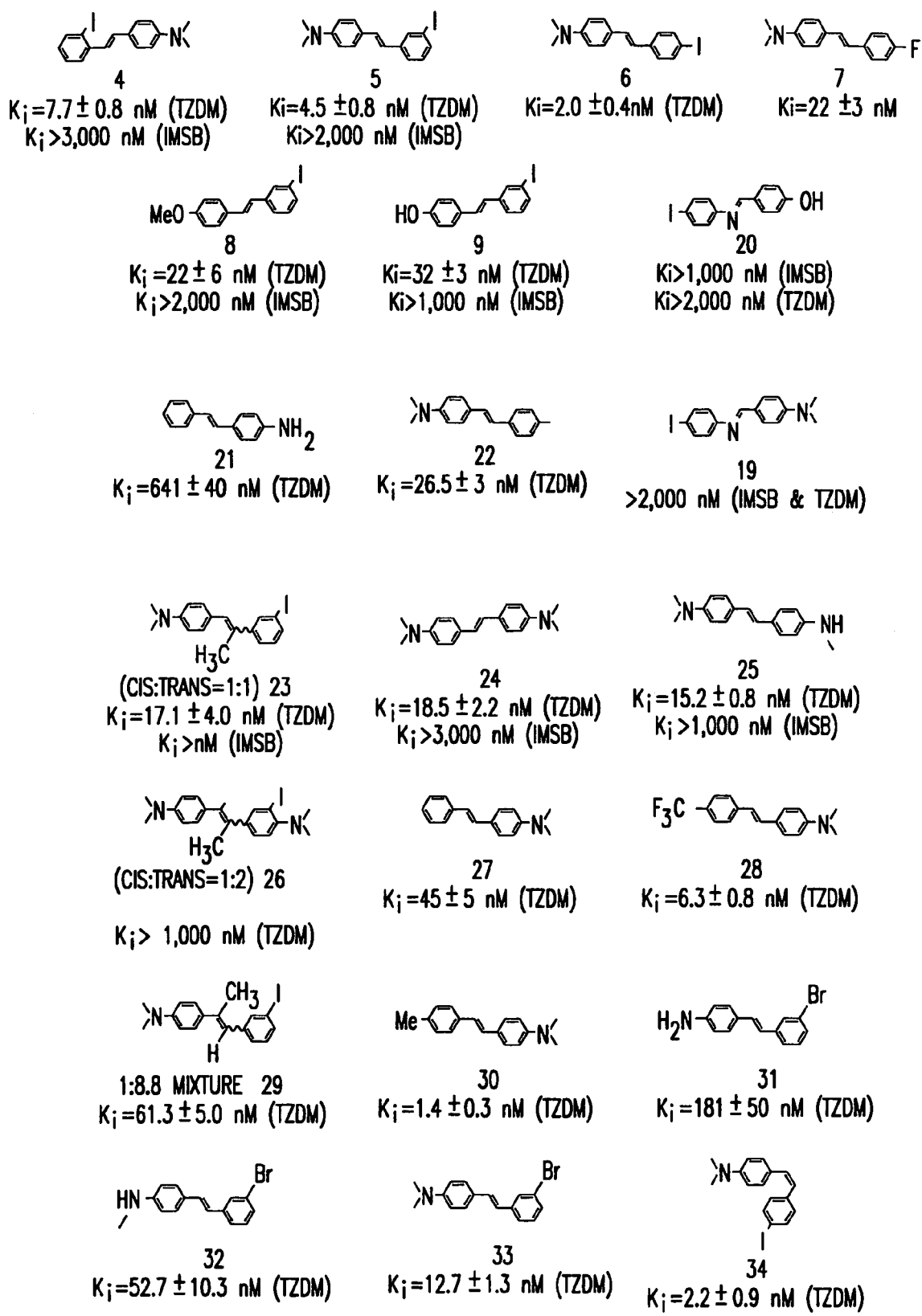
FIGS. 1, 3, 4 and 5 depict representative compounds of the present invention and the binding data for these compounds.

A first aspect of the present invention is directed to compounds of Formula I:

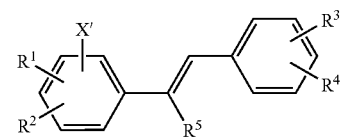

or a pharmaceutically acceptable salt thereof, wherein:

$R^5$ is hydrogen or $C_{1-4}$ alkyl;

$R^1$, $R^2$ and $R^3$, in each instance, is independently selected from the group consisting of hydrogen, halogen, $C_{1-4}$ alkyl, cyano, carboxy($C_{1-5}$)alkyl, trifluoromethyl, nitro, methylamino, dimethylamino, halo($C_{1-4}$)alkyl, and formyl;

$R^4$ is selected from the group consisting of:
  a. $C_{1-4}$ alkylthio,
  b. halo($C_{1-4}$)alkoxy,
  c. carboxy($C_{1-5}$)alkyl,
  d. hydroxy,
  e. $C_{1-4}$ alkoxy,
  f. $NR^6R^7$, wherein
    $R^6$ and $R^7$ are hydrogen, halo($C_{1-4}$)alkyl or $C_{1-4}$ alkyl,
  g. phenyl($C_{1-4}$)alkyl,
  h. $C_{6-10}$ aryl,
  i. heteroaryl,
  j. heterocycle,
  k. heterocycle($C_{1-4}$)alkyl, and
  l. $C_{3-6}$ cycloalkyl,
    wherein said phenyl($C_{1-4}$)alkyl, $C_{6-10}$ aryl, heteroaryl, heterocycle, heterocycle($C_{1-4}$)alkyl or $C_{3-6}$ cycloalkyl is substituted with one of the following: $C_{1-4}$ alkylthio, $C_{1-4}$ alkyl sulfonyl, methoxy, hydroxy, dimethylamino or methylamino; and, X' is $^{125}$I, $^{123}$I, $^{131}$I, $^{18}$F, Fluoro($C_{1-4}$)alkyl, [$^{18}$Fluoro($C_{1-4}$)alkyl]alkylamino, [$^{18}$Fluoro($C_{1-4}$)alkyl]amino, $^{76}$Br, $^{77}$Br or Sn(alkyl)$_3$.

Useful compounds falling within the scope of Formula I include compounds wherein $R^5$ is hydrogen or $C_{1-4}$ alkyl. Especially useful values of $R^5$ are hydrogen and methyl. The most useful value of $R^5$ is hydrogen.

Useful compounds are those of Formula I wherein $R^1$, $R^2$ and $R^3$, in each instance, is independently selected from the group as described above. Preferably, $R^3$ is hydrogen. In this preferred embodiment, it is especially preferred that $R^1$ and $R^2$ are independently selected from the group consisting of hydrogen and $C_{1-4}$ alkyl. More preferably, at least one of $R^1$ and $R^2$ is hydrogen. Most preferably, $R^1$ and $R^2$ are hydrogen.

Useful compounds of Formula I also include those compounds wherein $R^4$ is as described above. Preferable values of $R^4$ under the scope of $C_{6-10}$ aryl include phenyl, naphthyl or tetrahydronaphthyl. Preferable values of $R^4$ under the scope of heteroaryl include thienyl, furyl, pyranyl, pyrrolyl, pyridinyl, indolyl, and imidazolyl. Preferable values of $R^4$ under the scope of heterocycle include piperidinyl, pyrrolidinyl, and morpholinyl. In compounds wherein $R^4$ is a preferred embodiment of a $C_{6-10}$ aryl, heteroaryl, heterocycle, heterocycle($C_{1-4}$)alkyl or $C_{3-6}$ cycloalkyl, it is most preferable that the ring is substituted with one of the following: $C_{1-4}$ alkylthio, carboxy($C_{1-5}$)alkyl, hydroxy, methoxy, dimethylamino or methylamino. In another embodiment, $R^4$ is more preferably selected from the group consisting of $C_{1-4}$ alkylthio, halo($C_{1-4}$)alkoxy, carboxy($C_{1-5}$) alkyl, hydroxy, $C_{1-4}$ alkoxy, and $NR^6R^7$, wherein $R^6$ and $R^7$ are independently hydrogen, halo($C_{1-4}$)alkyl or $C_{1-4}$ alkyl. Most preferably, $R^4$ is selected from the group consisting of methylthio, carboxymethyl, carboxyethyl, carboxypropyl, hydroxy, methoxy, or $NR^6R^7$, wherein $R^6$ and $R^7$ are independently hydrogen, fluoro($C_{1-4}$)alkyl or methyl.

Useful values of X' include $^{125}I$, $^{123}I$, $^{131}I$, $^{18}F$, $^{18}$Fluoro$(C_{1-4})$alkyl, [$^{18}$Fluoro$(C_{1-4})$alkyl]alkylamino, [18 Fluoro$(C_{1-4})$alkyl]amino, $^{76}$Br, $^{77}$Br or Sn(alkyl)$_3$. Especially useful values of X' are $^{123}I$, $^{18}$Fluoromethyl, $^{18}$Fluoroethyl and $^{18}$Fluoropropyl.

The present invention is also directed to compounds of Formula II:

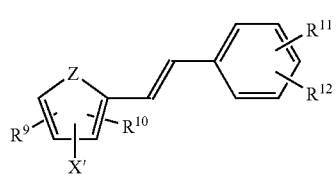

II or a pharmaceutically acceptable salt thereof,

Z is O, S or $NR^a$, wherein $R^a$ is $C_{1-4}$ alkyl;

$R^9$, $R^{10}$ and $R^{11}$, in each instance, is independently selected from the group consisting of hydrogen, halogen, $C_{1-4}$ alkyl, cyano, carboxy($C_{1-5}$)alkyl, trifluoromethyl, nitro, methylamino, dimethylamino, halo($C_{1-4}$)alkyl, and formyl;

$R^{12}$ is selected from the group consisting of:
a. $C_{1-4}$ alkylthio,
b. halo($C_{1-4}$)alkoxy,
c. carboxy($C_{1-5}$)alkyl,
d. hydroxy,
e. $C_{1-4}$ alkoxy,
f. $NR^{13}R^{14}$, wherein
   $R^{13}$ and $R^{14}$ are hydrogen, halo($C_{1-4}$)alkyl or $C_{1-4}$ alkyl,
g. phenyl($C_{1-4}$)alkyl,
h. $C_{6-10}$ aryl,
i. heteroaryl,
j. heterocycle,
k. heterocycle($C_{1-4}$)alkyl, and
l. $C_{3-6}$ cycloalkyl,
   wherein said phenyl($C_{1-4}$)alkyl, $C_{6-10}$ aryl, heteroaryl, heterocycle, heterocycle($C_{1-4}$)alkyl or $C_{3-6}$ cycloalkyl is substituted with one of the following:

$C_{1-4}$ alkylthio, $C_{1-4}$ alkyl sulfonyl, methoxy, hydroxy, dimethylamino or methylamino; and, X' is $^{125}I$, $^{123}I$, $^{131}I$, $^{18}F$, $^{18}$Fluoro$(C_{1-4})$alkyl, [$^{18}$Fluoro$(C_{1-4})$alkyl]alkylamino, [$^{18}$Fluoro$(C_{1-4})$alkyl]amino, $^{76}$Br, $^{77}$Br or Sn(alkyl)$_3$.

Useful compounds falling within the scope of Formula II include compounds wherein Z is O, S or $NR^a$, wherein $R^a$ is $C_{1-4}$ alkyl. Especially useful compounds are those wherein Z is O.

Useful compounds are those of Formula I wherein $R^9$, $R^{10}$ and $R^{11}$, in each instance, is independently selected from the group as described above. Preferably, $R^{11}$ is hydrogen. In this preferred embodiment, it is especially preferred that $R^9$ and $R^{10}$ are independently selected from the group consisting of hydrogen and $C_{1-4}$ alkyl. More preferably, at least one of $R^9$ and $R^{10}$ is hydrogen. Most preferably, $R^9$ and $R^{10}$ are hydrogen.

Useful compounds of Formula I also include those compounds wherein $R^{12}$ is as described above. Preferable values of $R^{12}$ under the scope of $C_{6-10}$ aryl include phenyl, naphthyl or tetrahydronaphthyl. Preferable values of $R^{12}$ under the scope of heteroaryl include thienyl, furyl, pyranyl, pyrrolyl, pyridinyl, indolyl, and imidazolyl. Preferable values of $R^{12}$ under the scope of heterocycle include piperidinyl, pyrrolidinyl, and morpholinyl. In compounds wherein $R^{12}$ is a preferred embodiment of a $C_{6-10}$ aryl, heteroaryl, heterocycle, heterocycle($C_{1-4}$)alkyl or $C_{3-6}$ cycloalkyl, it is most preferable that the ring is substituted with one of the following: $C_{1-4}$ alkylthio, carboxy($C_{1-5}$)alkyl, methoxy, hydroxy, dimethylamino or methylamino. In another embodiment, $R^{12}$ is more preferably selected from the group consisting of $C_{1-4}$ alkylthio, halo($C_{1-4}$)alkoxy, carboxy($C_{1-5}$) alkyl, hydroxy, $C_{1-4}$ alkoxy, and $NR^{13}R^{14}$, wherein $R^{13}$ and $R^{14}$ are independently hydrogen, halo($C_{1-4}$)alkyl or $C_{1-4}$alkyl. Most preferably, $R^{12}$ is selected from the group consisting of methylthio, carboxymethyl, carboxyethyl, carboxypropyl, hydroxy, methoxy, or $NR^{13}R^{14}$, wherein $R^{13}$ and $R^{14}$ are independently hydrogen, fluoro($C_{1-4}$)alkyl or methyl.

Useful values of X' include $^{125}I$, $^{123}I$, $^{131}I$, $^{18}F$, $^{18}$Fluoro$(C_{1-4})$alkyl, [$^{18}$Fluoro$(C_{1-4})$alkyl]alkylamino, [$^{18}$Fluoro$(C_{1-4})$alkyl]amino, $^{76}$Br, $^{77}$Br or Sn(alkyl)$_3$. Especially useful values of X' are $^{123}I$, $^{18}$Fluoromethyl, $^{18}$Fluoroethyl and $^{18}$Fluoropropyl.

Another aspect of the present invention is directed to compounds of Formula III:

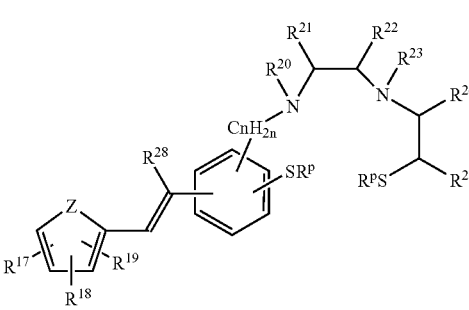

III or a pharmaceutically acceptable salt thereof, wherein:
n is equal to a number from zero to four,
$R^{28}$ is hydrogen or $C_{1-4}$ alkyl,
Z is O, S or —$CR^{15}$=$CR^{16}$—, wherein $R^{15}$, $R^{16}$, $R^{17}$, $R^{18}$, $R^{19}$, $R^{20}$, $R^{21}$, $R^{22}$, $R^{23}$, $R^{24}$ and $R^{25}$ in each instance, is independently selected from the group consisting of hydrogen, halogen, Sn(alkyl)$_3$, $C_{1-4}$ alkyl, $C_{1-4}$ alkyl sulfanyl, $C_{1-4}$ alkyl sulfonyl, $C_{1-4}$ alkoxy, hydroxy, $C_{6-10}$ aryl, carboxyalkyl, carboxy and $NR^{26}R^{27}$, wherein $R^{26}$ and $R^{27}$ are independently hydrogen, $C_{1-4}$ alkyl, phenyl($C_{1-4}$)alkyl, halo($C_{1-4}$)alkyl, haloaryl($C_{1-4}$)alkyl, $C_{6-10}$ aryl, heteroaryl, heterocycle, heterocycle($C_{1-4}$)alkyl or $C_{3-6}$ cycloalkyl, wherein said $C_{6-10}$ aryl, $C_{6-10}$ heteroaryl, heterocycle or $C_{3-6}$ cycloalkyl is unsubstituted or substituted with one of the following: $C_{1-4}$ alkylthio, $C_{1-4}$ alkyl sulfonyl, methoxy, hydroxy, dimethylamino or methylamino, and, $R^P$ is hydrogen or a sulfur protecting group, such as methoxymethyl, methoxyethoxymethyl, p-methoxybenzyl or benzyl.

The tetradentate metal ligand moiety of Formula III is capable of complexing with a metal, such as 99m-pertechnetate, as described herein to form metal chelates, exemplified by the following Formula:

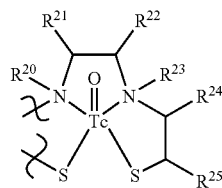

Additionally, a rhenium radioisotope can be complexed with the tetradentate metal ligand.

Useful compounds of Formula III are those compounds wherein Z is O, S or —$CR^{15}$=$CR^{16}$—, wherein $R^{15}$ and $R^{16}$ are as described above. Preferably, Z is —$CR^{15}$=$CR^{16}$—, wherein $R^{15}$ and $R^{16}$ are as described above. More preferably, $R^{15}$ and $R^{16}$ are hydrogen.

Useful compounds of the present invention are those compounds wherein $R^{17}$ through $R^{25}$ are as defined above. Preferable values of $R^{17}$ through $R^{25}$ falling under the scope of $C_{6-10}$ aryl include phenyl, naphthyl or tetrahydronaphthyl. Preferable values of $R^{17}$ through $R^{25}$ falling under the scope of heteroaryl include thienyl, furyl, pyranyl, pyrrolyl, pyridinyl, indolyl, and imidazolyl. Preferable values of $R^{17}$ through $R^{25}$ falling under the scope of heterocycle include piperidinyl, pyrrolidinyl, and morpholinyl. In compounds wherein $R^{17}$ through $R^{25}$ are a preferred embodiment of a $C_{6-10}$ aryl, heteroaryl, heterocycle, heterocycle($C_{1-4}$)alkyl or $C_{3-6}$ cycloalkyl, it is most preferable that the ring is substituted with one of the following: $C_{1-4}$ alkylthio, $C_{1-4}$ alkyl sulfonyl, methoxy, hydroxy, dimethylamino or methylamino. In another embodiment, more preferred compounds include those compounds wherein one or more of $R^{17}$ through $R^{25}$ is hydrogen. In this embodiment, it is preferred that $R^{17}$ is other than hydrogen. More preferably, $R^{17}$ is selected from the group consisting $C_{1-4}$ alkylthio, $C_{1-4}$ alkyl sulfonyl, hydroxy, $C_{1-4}$ alkoxy, $NR^{26}R^{27}$, wherein $R^{26}$ and $R^{27}$ are independently hydrogen or $C_{1-4}$ alkyl. Most preferably, $R^{17}$ is $NR^{26}R^{27}$, wherein $R^{26}$ and $R^{27}$ are methyl.

Useful compounds also include those of Formula III wherein n is equal to a number from zero to four. Preferably, n is equal to a number from zero to two. More preferably, n is equal to zero.

A further aspect of the present invention is directed to compounds of Formula IV:

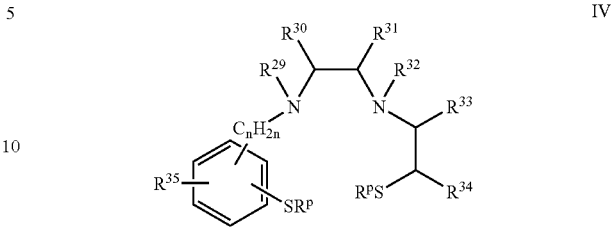

or a pharmaceutically acceptable salt thereof, wherein
n is equal to a number between zero and four,
$R^{29}$, $R^{30}$, $R^{31}$, $R^{32}$, $R^{33}$, $R^{34}$ and $R^3$ are independently selected from the group consisting of:
a. hydrogen,
b. $C_{1-4}$ alkylthio,
c. $C_{1-4}$ alkylsulfonyl,
d. hydroxy,
e. $C_{1-4}$ alkoxy,
f. $NR^6R^7$, wherein
$R^6$ and $R^7$ are hydrogen or $C_{1-4}$ alkyl,
g. phenyl($C_{1-4}$)alkyl,
h. $C_{6-10}$ aryl,
i. heteroaryl,
j. heterocycle,
k. heterocycle($C_{1-4}$)alkyl, and
l. $C_{3-6}$ cycloalkyl,
wherein said phenyl($C_{1-4}$)alkyl, $C_{6-10}$ aryl, heteroaryl, heterocycle, heterocycle($C_{1-4}$)alkyl or $C_{3-6}$ cycloalkyl is substituted with one of the following: $C_{1-4}$ alkylthio, $C_{1-4}$ alkyl sulfonyl, methoxy, hydroxy, dimethylamino or methylamino;
provided that one of $R^{29}$ through $R^{35}$ is monoalkylaminophenyl or dialkylaminophenyl; and
$R^P$ is hydrogen or a sulfur protecting group, such as methoxymethyl, methoxyethoxymethyl, p-methoxybenzyl or benzyl.

Useful compounds of Formula IV are those compounds wherein $R^{29}$, $R^{30}$, $R^{31}$, $R^{32}$, $R^{33}$, $R^{34}$ and $R^{35}$ are as described above. Preferable values of $R^{29}$ through $R^{35}$ falling under the scope of $C_{6-10}$ aryl include phenyl, naphthyl or tetrahydronaphthyl. Preferable values of $R^{29}$ through $R^{35}$ falling under the scope of heteroaryl include thienyl, furyl, pyranyl, pyrrolyl, pyridinyl, indolyl and imidazolyl. Preferable values of $R^{29}$ through $R^{35}$ falling under the scope of heterocycle include piperidinyl, pyrrolidinyl, and morpholinyl. In compounds wherein $R^{29}$ through $R^{35}$ are a preferred embodiment of a $C_{6-10}$ aryl, heteroaryl, heterocycle, heterocycle($C_{1-4}$)alkyl or $C_{3-6}$ cycloalkyl, it is most preferable that the ring is substituted with one of the following: $C_{1-4}$ alkylthio, $C_{1-4}$ alkyl sulfonyl, methoxy, hydroxy, dimethylamino or methylamino. In another embodiment, especially useful compounds are those wherein $R^{29}$, $R^{30}$, $R^{31}$, and $R^{33}$ are hydrogen. Within this embodiment, it is especially preferred that one of $R^{32}$ and $R^{34}$ is as described above, the other of $R^{32}$ and $R^{34}$ is hydrogen. More preferably, one of $R^{32}$ and $R^{34}$ is aminophenyl, monoalkylaminophenyl or dialkylaminophenyl, the other of $R^{32}$ and $R^{34}$ is hydrogen. Most preferably, one of $R^{32}$ and $R^{34}$ is dimethylaminophenyl, the other of $R^{32}$ and $R^{34}$ is hydrogen. Useful values of $R^{35}$ also include hydrogen, methoxy, $C_{1-4}$ alkylthio, $C_{1-4}$ alkyl sulfonyl, hydroxy and $C_{1-4}$ alkyl. Most preferably, $R^{35}$ is hydrogen or $C_{1-4}$ alkyl.

Useful compounds of Formula IV also include compounds wherein n is equal to a number from zero to four. More preferably, n is equal to zero or one. Most preferably, n is equal to zero.

It is also to be understood that the present invention is considered to include stereoisomers as well as optical isomers, e.g. mixtures of enantiomers as well as individual enantiomers and diastereomers, which arise as a consequence of structural asymmetry in selected compounds of the present series.

The compounds of Formula I, II, III or IV may also be solvated, especially hydrated. Hydration may occur during manufacturing of the compounds or compositions comprising the compounds, or the hydration may occur over time due to the hygroscopic nature of the compounds. In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

A further aspect of this invention is directed to compounds of Formula V:

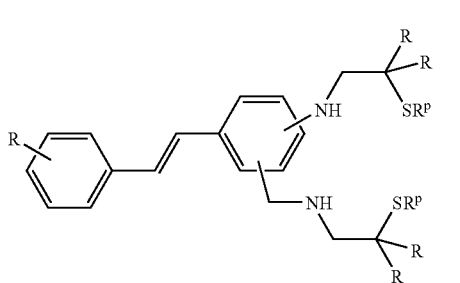

or a pharmaceutically acceptable salt thereof or a derivative of compound of Formula V containing a radioisotope complex, wherein:

R is $C_{1-4}$ alkyl or is as defined for $R^{29}$-$R^{35}$ above, and $R^P$ is as defined above.

When any variable occurs more than one time in any constituent or in Formula I, II, III, IV or V its definition on each occurrence is independent of its definition at every other occurrence. Also combinations of substituents and/or variables are permissible only if such combinations result in stable compounds.

The term "alkyl" as employed herein by itself or as part of another group refers to both straight and branched chain radicals of up to 8 carbons, preferably 6 carbons, more preferably 4 carbons, such as methyl, ethyl, propyl, isopropyl, butyl, t-butyl, and isobutyl.

The term "alkoxy" is used herein to mean a straight or branched chain alkyl radical, as defined above, unless the chain length is limited thereto, bonded to an oxygen atom, including, but not limited to, methoxy, ethoxy, n-propoxy, isopropoxy, and the like. Preferably the alkoxy chain is 1 to 6 carbon atoms in length, more preferably 1-4 carbon atoms in length.

The term "monoalkylamine" as employed herein by itself or as part of another group refers to an amino group which is substituted with one alkyl group as defined above.

The term "dialkylamine" as employed herein by itself or as part of another group refers to an amino group which is substituted with two alkyl groups as defined above.

The term "halo" employed herein by itself or as part of another group refers to chlorine, bromine, fluorine or iodine.

The term "haloalkyl" as employed herein refers to any of the above alkyl groups substituted by one or more chlorine, bromine, fluorine or iodine with fluorine and chlorine being preferred, such as chloromethyl, iodomethyl, trifluoromethyl, 2,2,2-trifluoroethyl, and 2-chloroethyl.

The term "alkylthio" as employed herein by itself or as part of another group refers to a thioether of the structure: R—S, wherein R is a $C_{1-4}$ alkyl as defined above.

The term "alkylsulfonyl" as employed herein by itself or as part of another group refers to a sulfone of the structure: R—SO$_2$, wherein R is a $C_{1-4}$ alkyl as defined above.

The term "aryl" as employed herein by itself or as part of another group refers to monocyclic or bicyclic aromatic groups containing from 6 to 12 carbons in the ring portion, preferably 6-10 carbons in the ring portion, such as phenyl, naphthyl or tetrahydronaphthyl.

The term "heterocycle" or "heterocyclic ring", as used herein except where noted, represents a stable 5- to 7-membered mono-heterocyclic ring system which may be saturated or unsaturated, and which consists of carbon atoms and from one to three heteroatoms selected from the group consisting of N, O, and S, and wherein the nitrogen and sulfur heteroatom may optionally be oxidized. Especially useful are rings contain one nitrogen combined with one oxygen or sulfur, or two nitrogen heteroatoms. Examples of such heterocyclic groups include piperidinyl, pyrrolyl, pyrrolidinyl, imidazolyl, imidazinyl, imidazolidinyl, pyridyl, pyrazinyl, pyrimidinyl, oxazolyl, oxazolidinyl, isoxazolyl, isoxazolidinyl, thiazolyl, thiazolidinyl, isothiazolyl, homopiperidinyl, homopiperazinyl, pyridazinyl, pyrazolyl, and pyrazolidinyl, most preferably thiamorpholinyl, piperazinyl, and morpholinyl.

The term "heteroatom" is used herein to mean an oxygen atom ("O"), a sulfur atom ("S") or a nitrogen atom ("N"). It will be recognized that when the heteroatom is nitrogen, it may form an $NR^aR^b$ moiety, wherein $R^a$ and $R^b$ are, independently from one another, hydrogen or $C_{1-4}$ alkyl, $C_{2-4}$ aminoalkyl, $C_{1-4}$ halo alkyl, halo benzyl, or $R^1$ and $R^2$ are taken together to form a 5- to 7-member heterocyclic ring optionally having O, S or $NR^c$ in said ring, where $R^c$ is hydrogen or $C_{1-4}$ alkyl.

The term "heteroaryl" as employed herein refers to groups having 5 to 14 ring atoms; 6, 10 or 14π electrons shared in a cyclic array; and containing carbon atoms and 1, 2 or 3 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4aH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl and phenoxazinyl groups).

The term "aralkyl" or "arylalkyl" as employed herein by itself or as part of another group refers to $C_{1-6}$alkyl groups as discussed above having an aryl substituent, such as benzyl, phenylethyl or 2-naphthylmethyl.

Another aspect of this invention is related to methods of preparing compounds of Formula I, II, III, IV or V.

In embodiments of Formulae III, IV or V, the groups $R^P$ are both hydrogen, or can be any of the variety of protecting groups available for sulfur, including methoxymethyl, methoxyethoxymethyl, p-methoxybenzyl or benzyl. Sulfur protecting groups are described in detail in Greene, T. W. and Wuts, P. G. M., *Protective Groups in Organic Synthesis*, 2nd Edition, John Wiley and Sons, Inc., New York (1991). Protecting group $R^P$ can be removed by appropriate methods well known in the art of organic synthesis, such as trifluoroacetic acid, mercuric chloride or sodium in liquid ammonia. In the case of Lewis acid labile groups, including acetamidomethyl and benzamidomethyl, $R^P$ can be left intact. Labeling of the ligand with technetium in this case will cleave the protecting group, rendering the protected diaminedithiol equivalent to the unprotected form.

Tc-99m complexes can be prepared as follows. A small amount of non-radiolabeled compound (1-2 mg) is dissolved in 100 μL EtOH and mixed with 200 μL HCl (1 N) and 1 mL Sn-glucoheptonate solution (containing 8-32 μg $SnCl_2$ and 80-320 μg Na-glucoheptonate, pH 6.67) and 50 μL EDTA solution (0.1 N). [$^{99m}$Tc]Pertechnetate (100-200 μL; ranging from 2-20 mCi) saline solution are then added. The reaction is heated for 30 min at 100° C., then cooled to room temperature. The reaction mixture is analyzed on TLC (EtOH:conc. $NH_3$ 9:1) for product formation and purity check. The mixture can be neutralized with phosphate buffer to pH 5.0.

The present invention further relates to a method of preparing a technetium-99 m complex according to the present invention by reacting technetium-99 m in the form of a pertechnetate in the presence of a reducing agent and optionally a suitable chelator with an appropriate Ch-containing compound.

The reducing agent serves to reduce the Tc-99 m pertechnetate which is eluted from a molybdenum-technetium generator in a physiological saline solution. Suitable reducing agents are, for example, dithionite, formamidine sulphinic acid, diaminoethane disulphinate or suitable metallic reducing agents such as Sn(II), Fe(II), Cu(I), Ti(III) or Sb(III). Sn(II) has proven to be particularly suitable.

For the above-mentioned complex-forming reaction, technetium-99 m is reacted with an appropriate compound of the invention as a salt or in the form of technetium bound to comparatively weak chelators. In the latter case the desired technetium-99 m complex is formed by ligand exchange. Examples of suitable chelators for the radionuclide are dicarboxylic acids, such as oxalic acid, malonic acid, succinic acid, maleic acid, orthophtalic acid, malic acid, lactic acid, tartaric acid, citric acid, ascorbic acid, salicylic acid or derivatives of these acids; phosphorus compounds such as pyrophosphates; or enolates. Citric acid, tartaric acid, ascorbic acid, glucoheptonic acid or a derivative thereof are particularly suitable chelators for this purpose, because a chelate of technetium-99 m with one of these chelators undergoes the desired ligand exchange particularly easily.

The most commonly used procedure for preparing [$Tc^VO$]$^{+3}N_2S_2$ complexes is based on stannous (II) chloride reduction of [$^{99m}$Tc]pertechnetate, the common starting material. The labeling procedure normally relies on a Tc-99 m ligand exchange reaction between Tc-99 m (Sn)-glucoheptonate and the $N_2S_2$ ligand. Preparation of stannous (II) chloride and preserving it in a consistent stannous (II) form is critically important for the success of the labeling reaction. To stabilize the air-sensitive stannous ion it is a common practice in nuclear medicine to use a lyophilized kit, in which the stannous ion is in a lyophilized powder form mixed with an excess amount of glucoheptonate under an inert gas like nitrogen or argon. The preparation of the lyophilized stannous chloride/sodium glucoheptonate kits ensures that the labeling reaction is reproducible and predictable. The $N_2S_2$ ligands are usually air-sensitive (thiols are easily oxidized by air) and there are subsequent reactions which lead to decomposition of the ligands. The most convenient and predictable method to preserve the ligands is to produce lyophilized kits containing 100-500 μg of the ligands under argon or nitrogen.

The present invention is further directed to methods of preparing compounds of the above Formula I, II, III, IV or V. The compounds of this invention can be prepared by reactions described in Schemes 1-9.

Schemes 1-5 depict a synthetic route for forming stilbene derivatives of Formula I using a Wittig reagent.

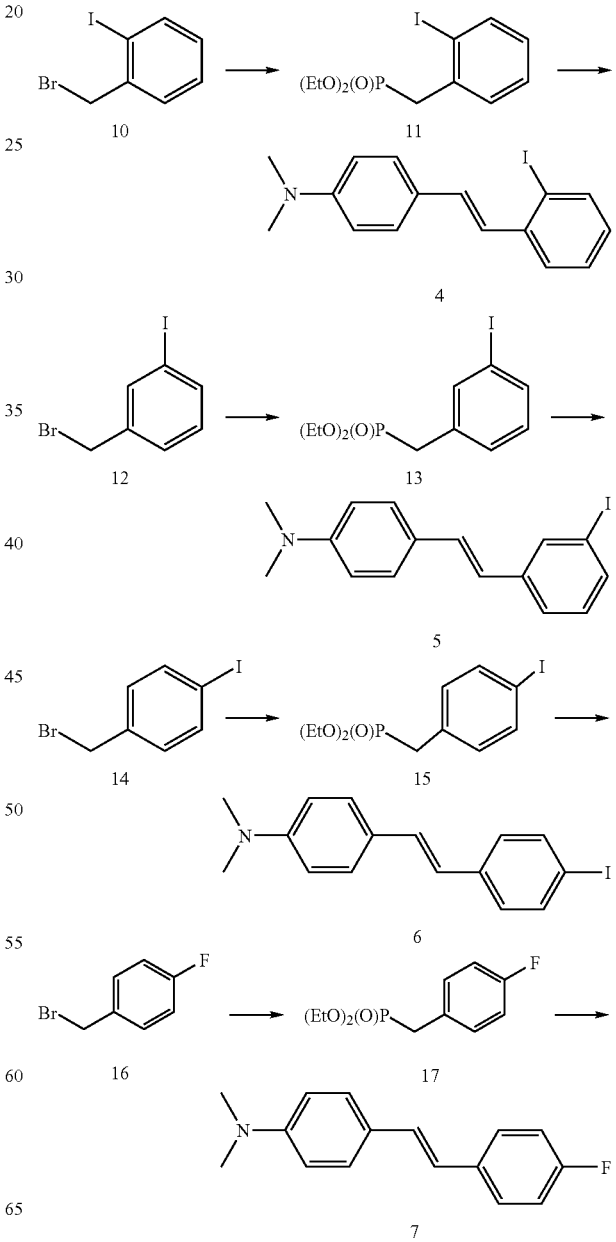

SCHEME 1

-continued
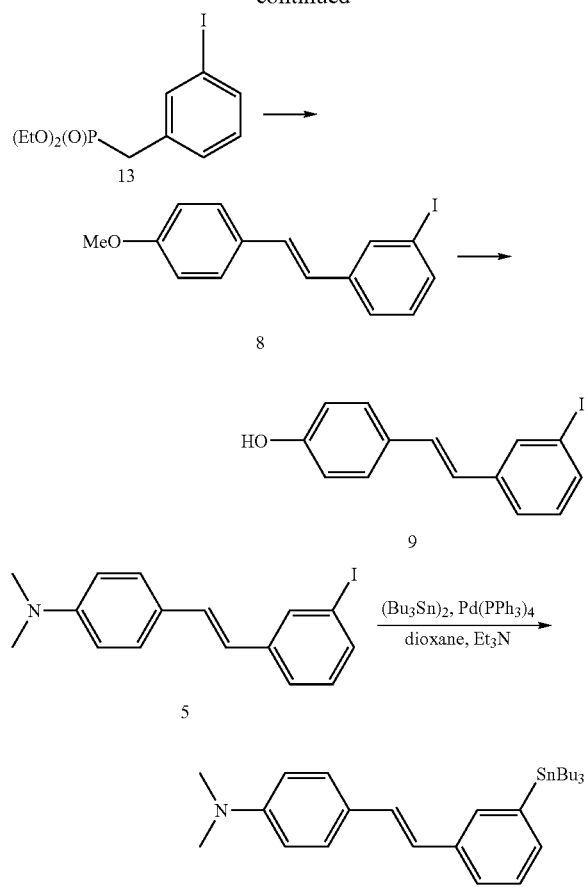
SCHEME 2
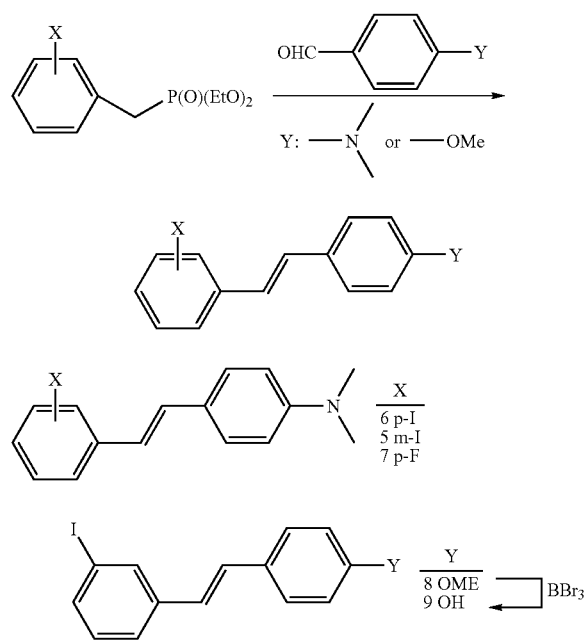
SCHEME 3
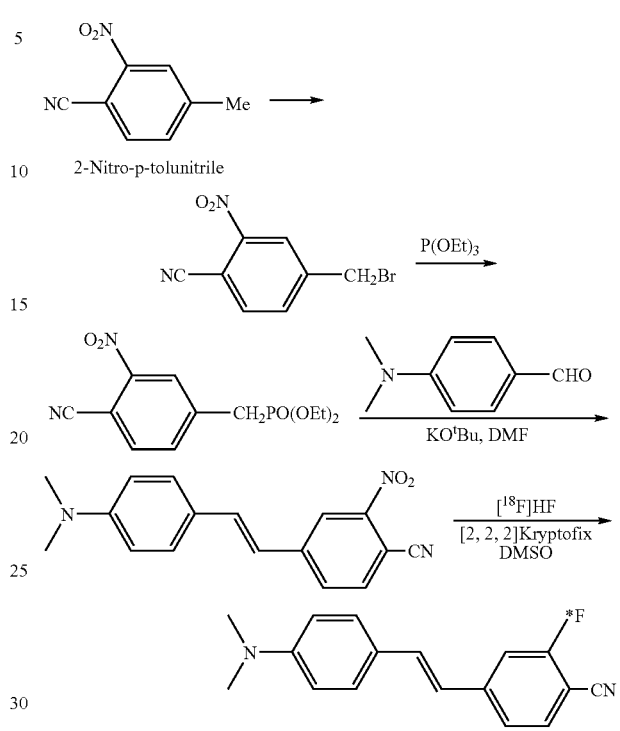
SCHEME 4
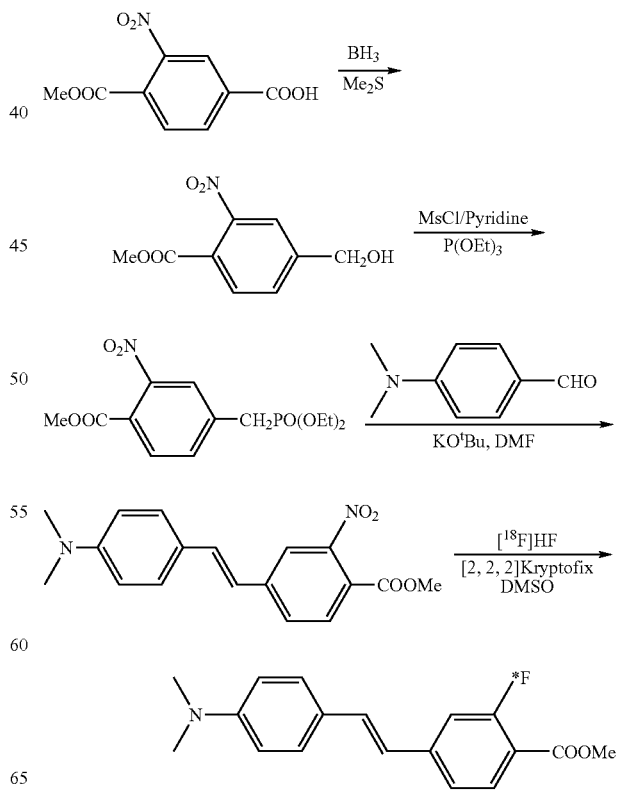

SCHEME 5
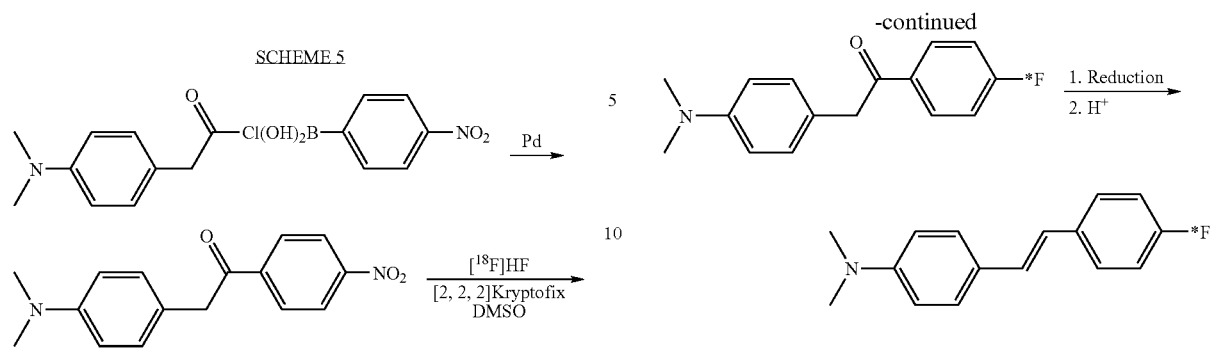
Scheme 6 depicts a synthetic route for forming derivatives of Formula II.
SCHEME 6
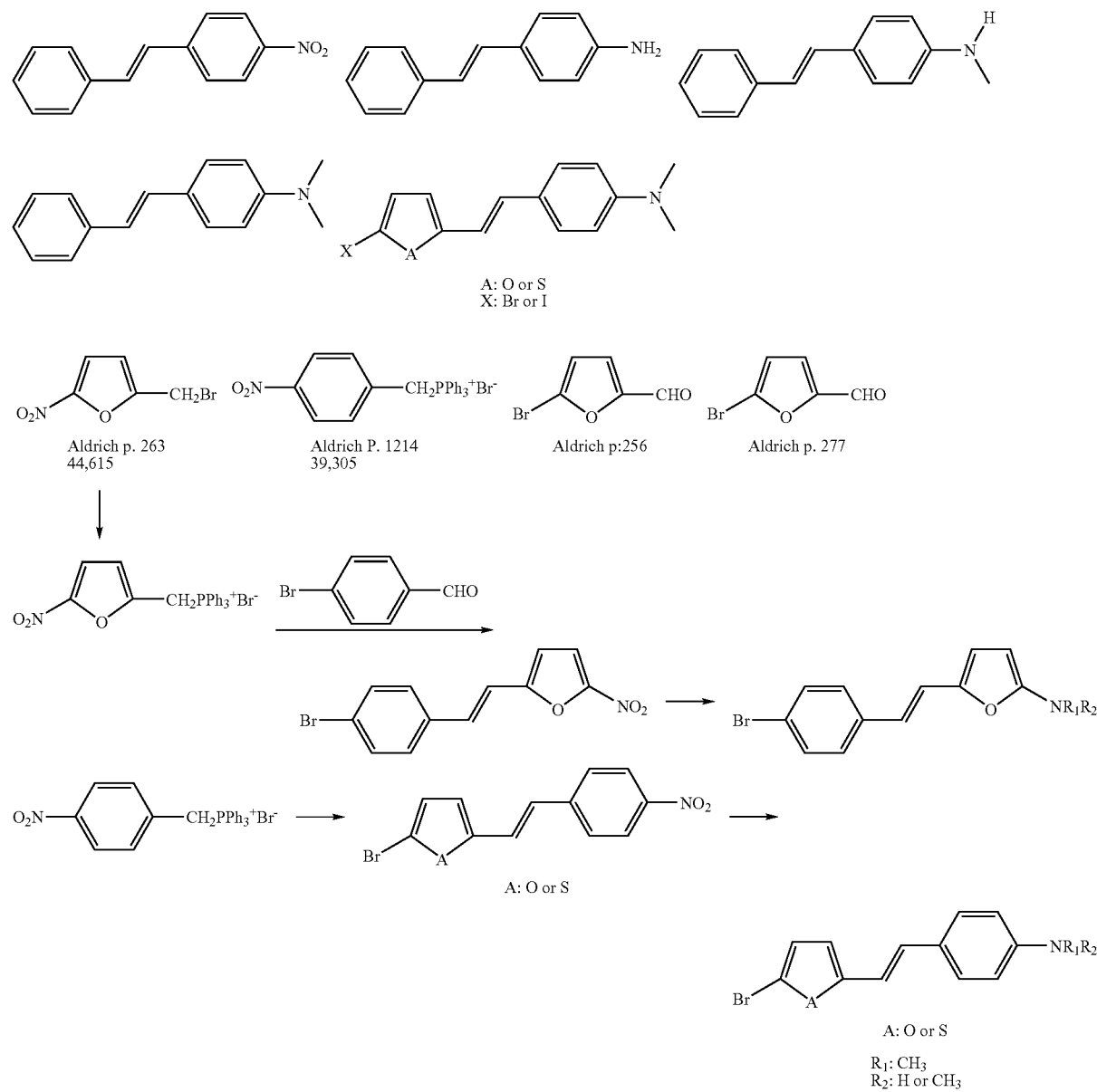

Scheme 7 depicts a synthetic route for forming derivatives of Formula III.
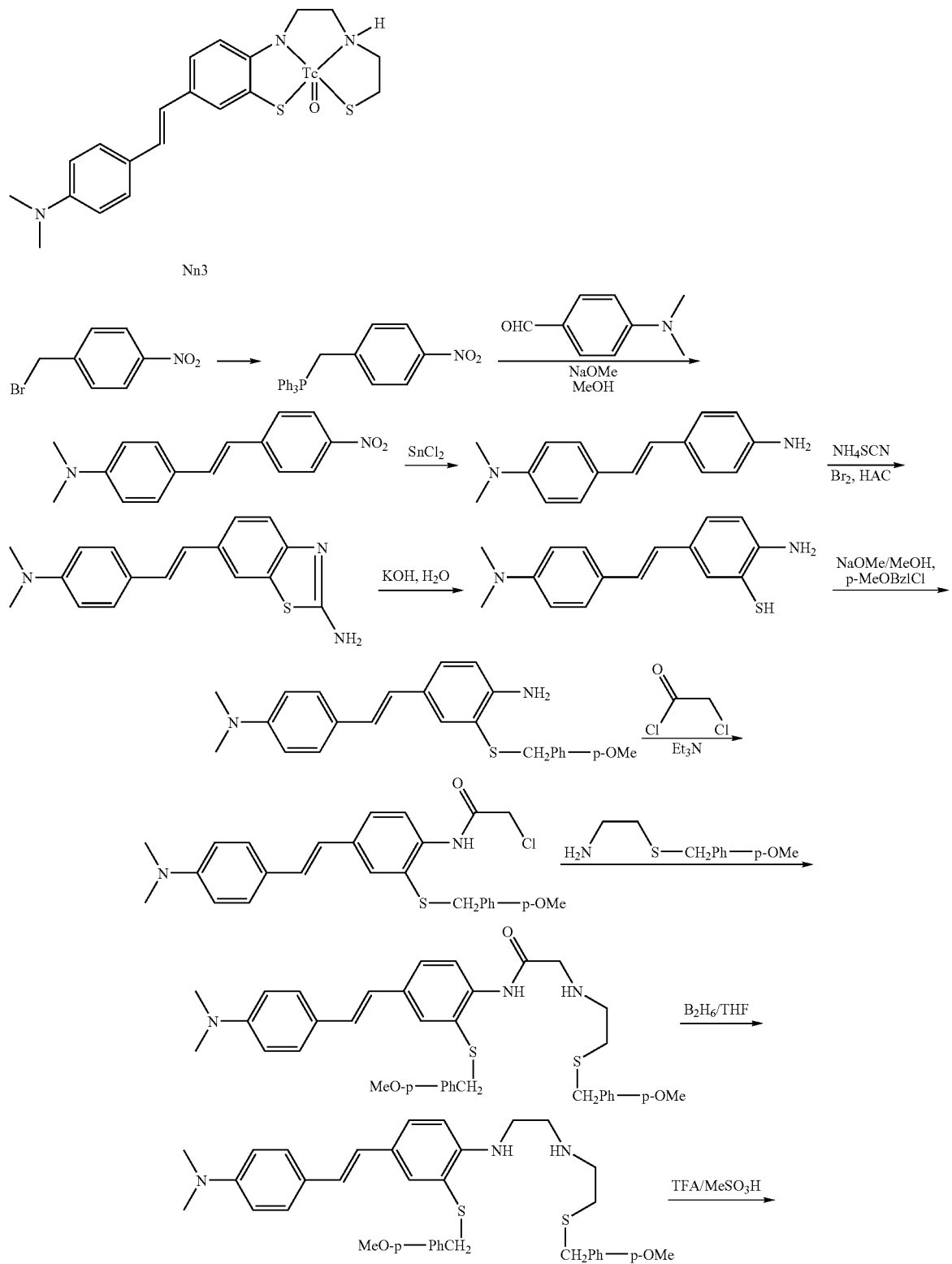

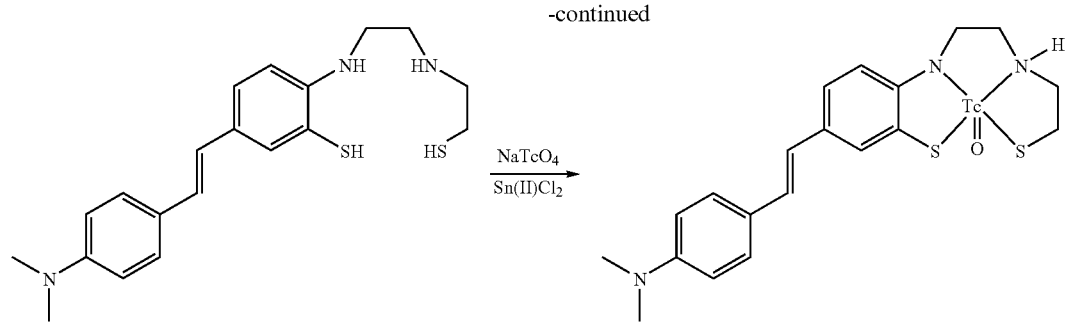
Scheme 8 depicts a synthetic route for derivatives of Formula IV.
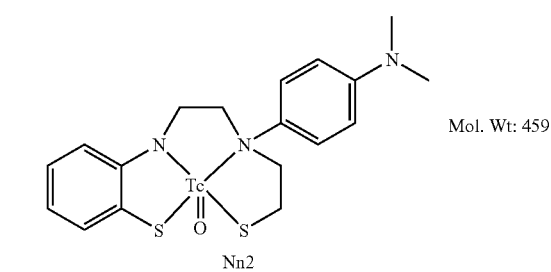
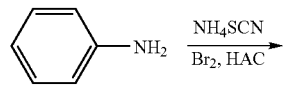
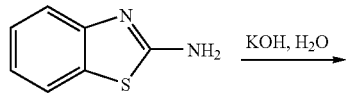
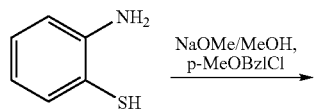
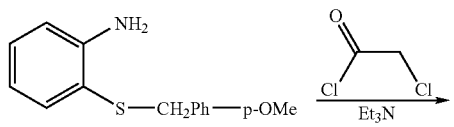
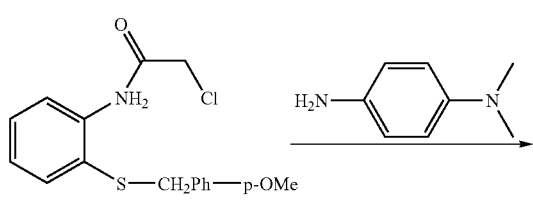
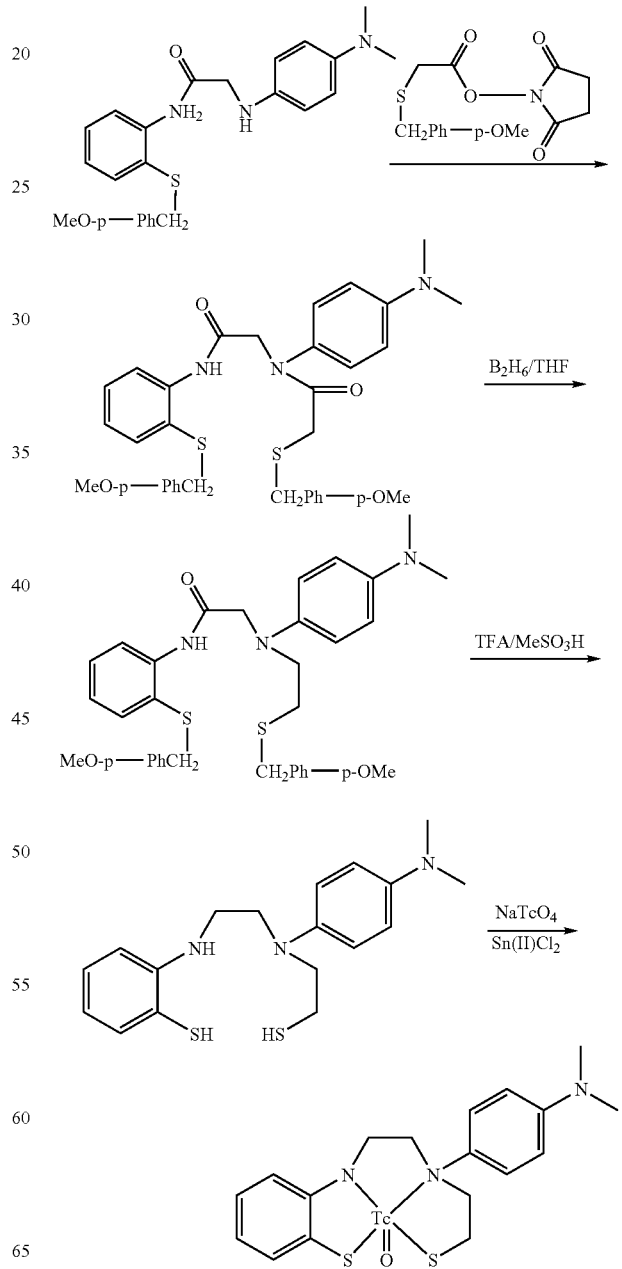

Scheme 9 depicts a synthetic route for forming derivatives of Formula IV.
SCHEME 9
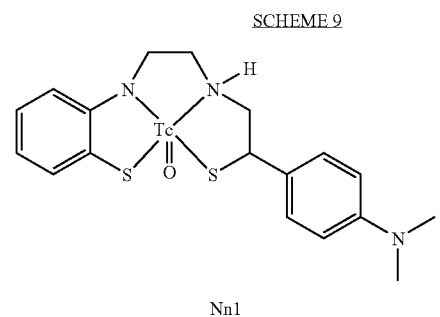
Nn1  Mol. Wt: 459.43
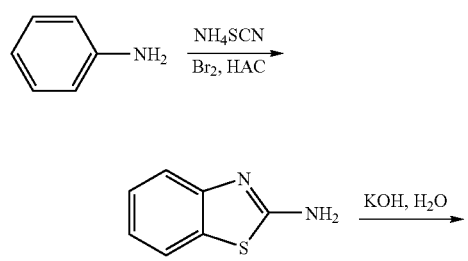
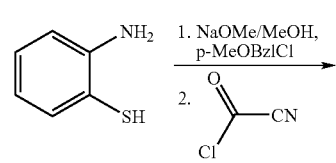
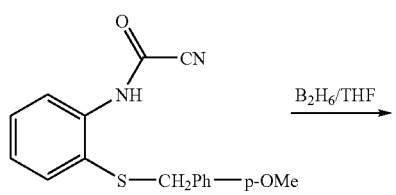
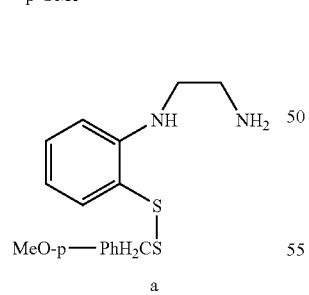
a
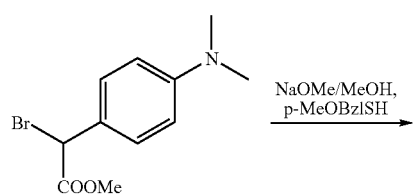
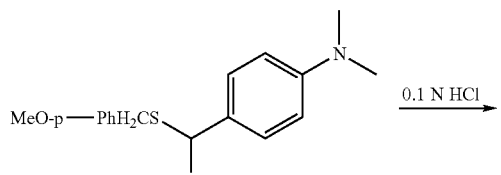
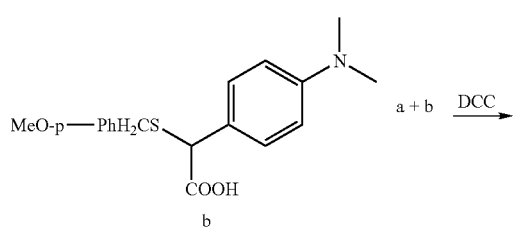
b
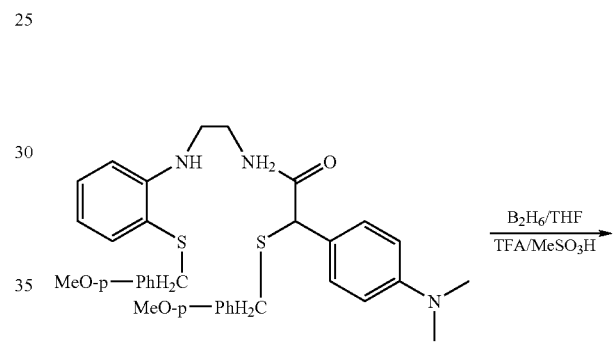
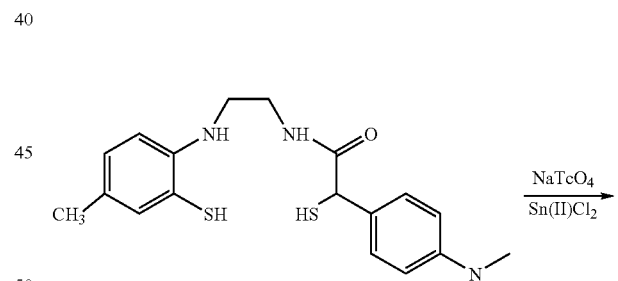
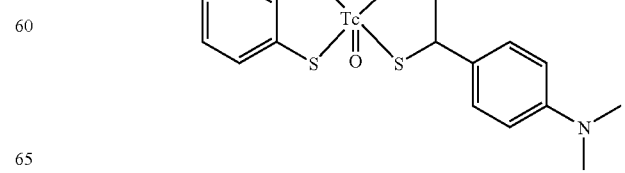

Schemes 10 and 11 depict synthetic routes for forming derivatives of Formula I.
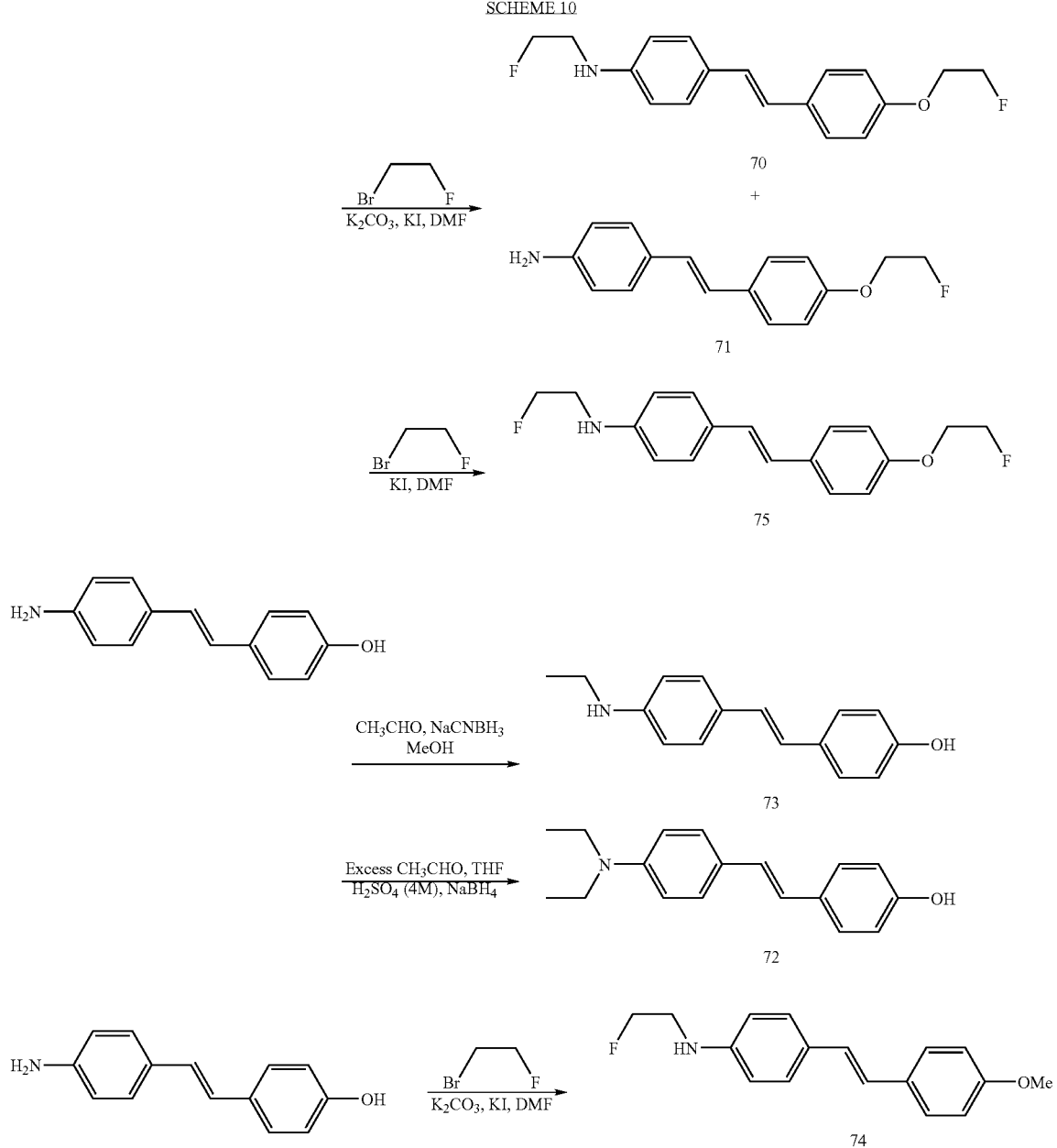
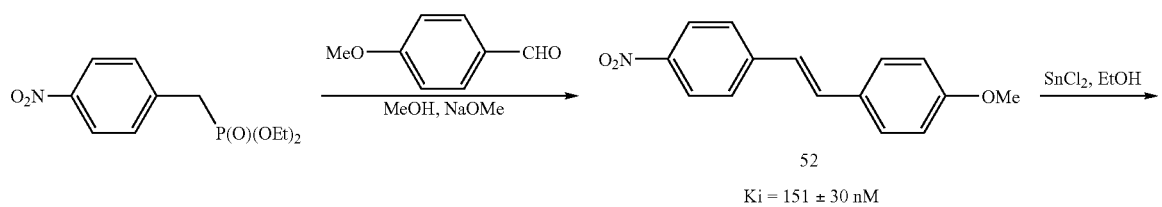

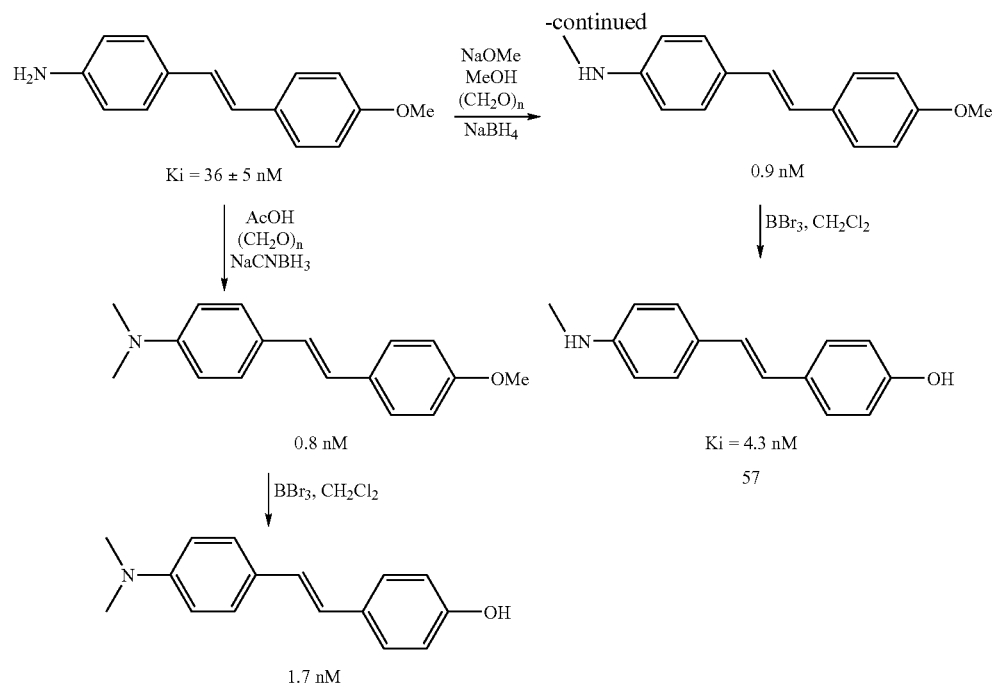
Scheme 12 depicts a synthetic route for forming intermediates of Formula V.
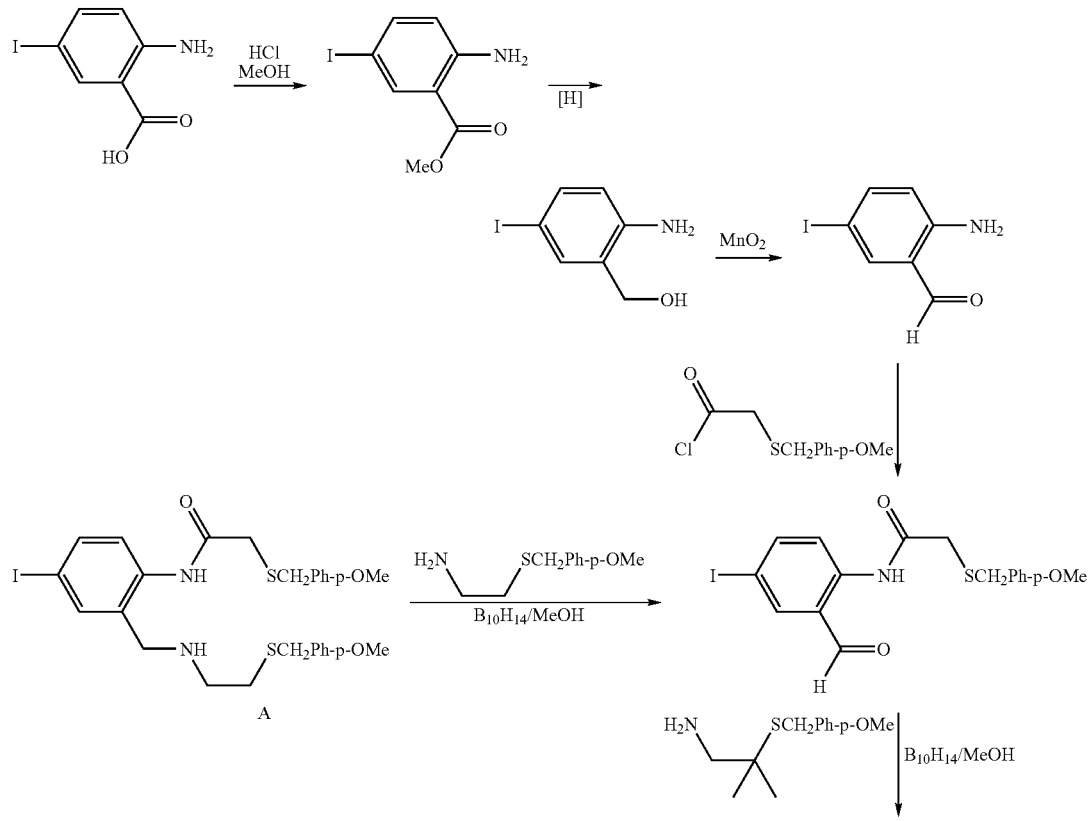

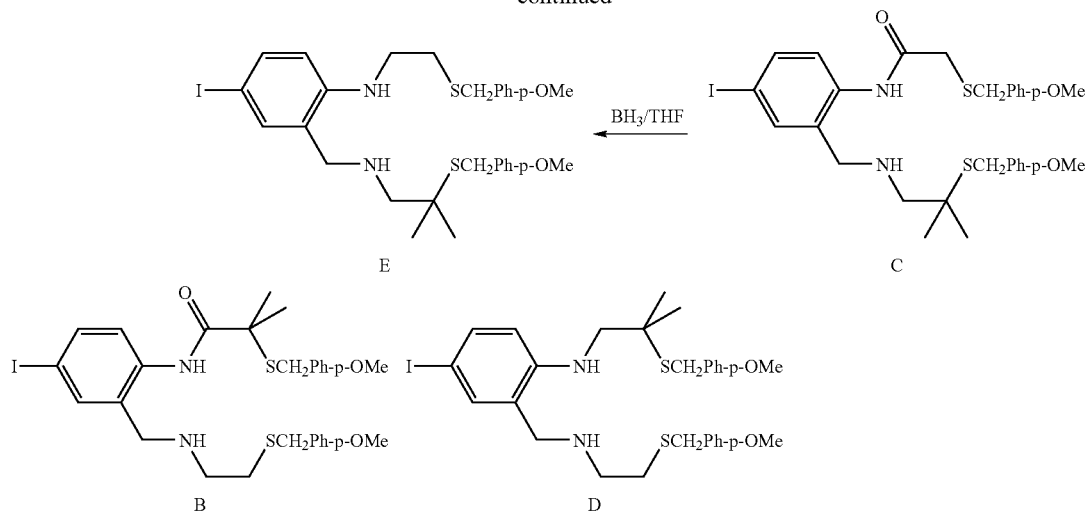
Scheme 13 depicts a synthetic route for forming derivatives of Formula V.
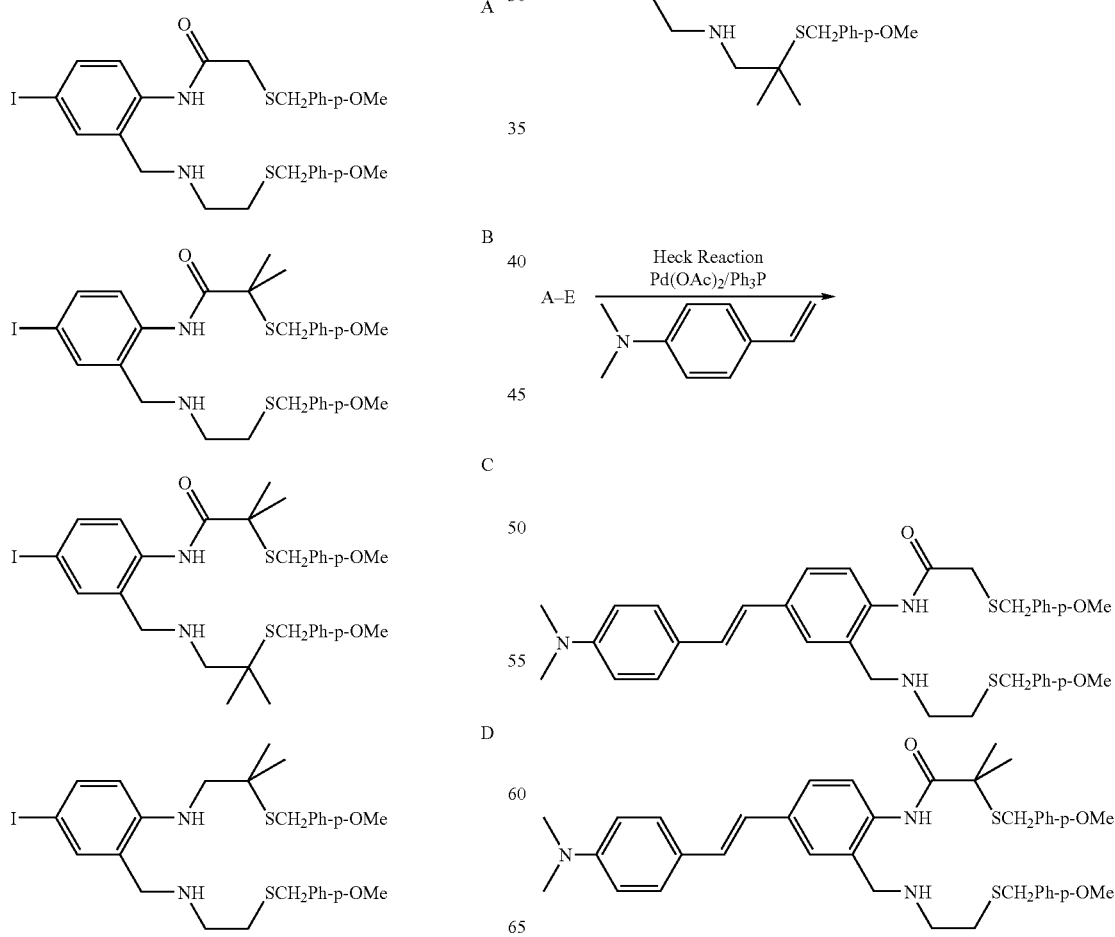

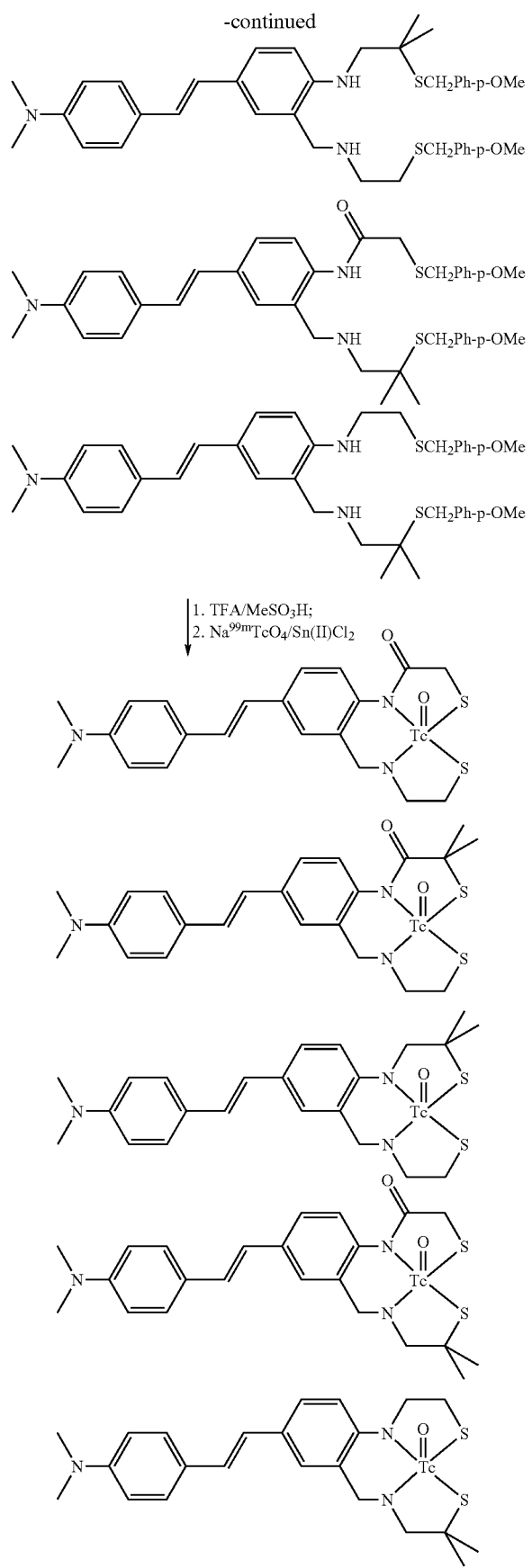

When the compounds of this invention are to be used as imaging agents, they must be labeled with suitable radioactive halogen isotopes. Although $^{125}$I-isotopes are useful for laboratory testing, they will generally not be useful for actual diagnostic purposes because of the relatively long half-life (60 days) and low gamma-emission (30-65 Kev) of $^{125}$I. The isotope $^{123}$I has a half life of thirteen hours and gamma energy of 159 KeV, and it is therefore expected that labeling of ligands to be used for diagnostic purposes would be with this isotope. Other isotopes which may be used include $^{131}$I (half life of 2 hours). Suitable bromine isotopes include $^{77}$Br and $^{76}$Br.

The radiohalogenated compounds of this invention lend themselves easily to formation from materials which could be provided to users in kits. Kits for forming the imaging agents can contain, for example, a vial containing a physiologically suitable solution of an intermediate of Formula I, II, III, IV or V in a concentration and at a pH suitable for optimal complexing conditions. The user would add to the vial an appropriate quantity of the radioisotope, e.g., Na$^{123}$I, and an oxidant, such as hydrogen peroxide. The resulting labeled ligand may then be administered intravenously to a patient, and receptors in the brain imaged by means of measuring the gamma ray or photo emissions therefrom.

Since the radiopharmaceutical composition according to the present invention can be prepared easily and simply, the preparation can be carried out readily by the user. Therefore, the present invention also relates to a kit, comprising:

(1) A non-radiolabeled compound of the invention, the compound optionally being in a dry condition; and also optionally having an inert, pharmaceutically acceptable carrier and/or auxiliary substances added thereto; and (2) a reducing agent and optionally a chelator;

wherein ingredients (1) and (2) may optionally be combined; and further wherein instructions for use with a prescription for carrying out the above-described method by reacting ingredients (1) and (2) with technetium-99 m in the form of a pertechnetate solution may be optionally included.

Examples of suitable reducing agents and chelators for the above kit have been listed above. The pertechnetate solution can be obtained by the user from a molybdenum-technetium generator. Such generators are available in a number of institutions that perform radiodiagnostic procedures. As noted above the ingredients (1) and (2) may be combined, provided they are compatible. Such a monocomponent kit, in which the combined ingredients are preferably lyophilized, is excellently suitable to be reacted by the user with the pertechnetate solution in a simple manner.

When desired, the radioactive diagnostic agent may contain any additive such as pH controlling agents (e.g., acids, bases, buffers), stabilizers (e.g., ascorbic acid) or isotonizing agents (e.g., sodium chloride).

The term "pharmaceutically acceptable salt" as used herein refers to those carboxylate salts or acid addition salts of the compounds of the present invention which are, within the scope of sound medical judgement, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively nontoxic, inorganic and organic acid addition salts of compounds of the present invention. Also included are those salts derived from nontoxic organic acids such as aliphatic mono and dicarboxylic acids, for example acetic acid, phenyl-substituted alkanoic acids, hydroxy alkanoic and alkanedioic acids, aromatic acids, and aliphatic and aromatic sulfonic acids. These salts can be prepared in situ during the final isolation and purification of the compounds or by separately reacting the purified compound in its free base form with a suitable organic or inorganic acid and isolating the salt thus formed. Further representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactiobionate and laurylsulphonate salts, propionate, pivalate, cyclamate, isethionate, and the like. These may include cations based on the alkali and alkaline earth metals, such as sodium, lithium, potassium, calcium, magnesium, and the like, as well as, nontoxic ammonium, quaternary ammonium and amine cations including, but not limited to ammonium, tetramethylammonium, tetraethylammonium, methylamine, dimethylamine, trimethylamine, triethylamine, ethylamine, and the like. (See, for example, Berge S. M., et al., *Pharmaceutical Salts, J. Pharm. Sci.* 66:1-19 (1977) which is incorporated herein by reference.)

In the first step of the present method of imaging, a labeled compound of Formula I, II, III, IV or V is introduced into a tissue or a patient in a detectable quantity. The compound is typically part of a pharmaceutical composition and is administered to the tissue or the patient by methods well known to those skilled in the art.

For example, the compound can be administered either orally, rectally, parenterally (intravenous, by intramuscularly or subcutaneously), intracisternally, intravaginally, intraperitoneally, intravesically, locally (powders, ointments or drops), or as a buccal or nasal spray.

In a preferred embodiment of the invention, the labeled compound is introduced into a patient in a detectable quantity and after sufficient time has passed for the compound to become associated with amyloid deposits, the labeled compound is detected noninvasively inside the patient. In another embodiment of the invention, a labeled compound of Formula I, II, III, IV or V is introduced into a patient, sufficient time is allowed for the compound to become associated with amyloid deposits, and then a sample of tissue from the patient is removed and the labeled compound in the tissue is detected apart from the patient. In a third embodiment of the invention, a tissue sample is removed from a patient and a labeled compound of Formula I, II, III, IV or V is introduced into the tissue sample. After a sufficient amount of time for the compound to become bound to amyloid deposits, the compound is detected.

The administration of the labeled compound to a patient can be by a general or local administration route. For example, the labeled compound may be administered to the patient such that it is delivered throughout the body. Alternatively, the labeled compound can be administered to a specific organ or tissue of interest. For example, it is desirable to locate and quantitate amyloid deposits in the brain in order to diagnose or track the progress of Alzheimer's disease in a patient.

The term "tissue" means a part of a patient's body. Examples of tissues include the brain, heart, liver, blood vessels, and arteries. A detectable quantity is a quantity of labeled compound necessary to be detected by the detection method chosen. The amount of a labeled compound to be introduced into a patient in order to provide for detection can readily be determined by those skilled in the art. For example, increasing amounts of the labeled compound can be given to a patient until the compound is detected by the detection method of choice. A label is introduced into the compounds to provide for detection of the compounds.

The term "patient" means humans and other animals. Those skilled in the art are also familiar with determining the amount of time sufficient for a compound to become associated with amyloid deposits. The amount of time necessary can easily be determined by introducing a detectable amount of a labeled compound of Formula I, II, III, IV or V into a patient and then detecting the labeled compound at various times after administration.

The term "associated" means a chemical interaction between the labeled compound and the amyloid deposit. Examples of associations include covalent bonds, ionic bonds, hydrophilic-hydrophilic interactions, hydrophobic-hydrophobic interactions, and complexes.

Those skilled in the art are familiar with the various ways to detect labeled compounds. For example, magnetic resonance imaging (MRI), positron emission tomography (PET), or single photon emission computed tomography (SPECT) can be used to detect radiolabeled compounds. The label that is introduced into the compound will depend on the detection method desired. For example, if PET is selected as a detection method, the compound must possess a positron-emitting atom, such as $^{11}C$ or $^{18}F$.

The radioactive diagnostic agent should have sufficient radioactivity and radioactivity concentration which can assure reliable diagnosis. For instance, in case of the radioactive metal being technetium-99 m, it may be included usually in an amount of 0.1 to 50 mCi in about 0.5 to 5.0 ml at the time of administration. The amount of a compound of Formula I, II, III, IV or V may be such as sufficient to form a stable chelate compound with the radioactive metal.

The thus formed chelate compound as a radioactive diagnostic agent is sufficiently stable, and therefore it may be immediately administered as such or stored until its use. When desired, the radioactive diagnostic agent may contain any additive such as pH controlling agents (e.g., acids, bases, buffers), stabilizers (e.g., ascorbic acid) or isotonizing agents (e.g., sodium chloride).

The imaging of amyloid deposits can also be carried out quantitatively so that the amount of amyloid deposits can be determined.

Preferred compounds for imaging include a radioisotope such as $^{123}I$, $^{125}I$, $^{131}I$, $^{18}F$, $^{76}Br$ or $^{77}Br$.

The present invention is also directed at a method of imaging amyloid deposits. One of the key prerequisites for an in vivo imaging agent of the brain is the ability to cross the intact blood-brain barrier after a bolus iv injection.

Another aspect of the invention is a method of inhibiting amyloid plaque aggregation. The present invention also provides a method of inhibiting the aggregation of amyloid proteins to form amyloid deposits, by administering to a patient an amyloid inhibiting amount of a compound of the above Formula I, II, III, IV or V.

Those skilled in the art are readily able to determine an amyloid inhibiting amount by simply administering a compound of Formula I, II, III, IV or V to a patient in increasing amounts until the growth of amyloid deposits is decreased or stopped. The rate of growth can be assessed using imaging as described above or by taking a tissue sample from a patient and observing the amyloid deposits therein. The compounds of the present invention can be administered to a patient at dosage levels in the range of about 0.1 to about 1,000 mg per day. For a normal human adult having a body weight of about 70 kg, a dosage in the range of about 0.01 to about 100 mg per kilogram of body weight per day is sufficient. The specific dosage used, however, can vary. For example, the dosage can depend on a number of factors including the requirements of the patient, the severity of the condition being treated, and the pharmacological activity of the compound being used. The determination of optimum dosages for a particular patient is well known to those skilled in the art.

The following examples are illustrative, but not limiting, of the method and compositions of the present invention. Other suitable modifications and adaptations of the variety of conditions and parameters normally encountered and obvious to those skilled in the art are within the spirit and scope of the invention.

EXAMPLE 1

Diethyl 2-iodobenzylphosphonate (11)

A mixture of 2-iodobenzyl bromide 10 (5 g, 16.84 mmol) and triethyl phosphite (3.3 g, 20 mmol) was stirred at 160° C. After 4 h, the mixture was cooled to room temperature. The residue was subjected to flash chromatography (EtOAc: Hex, 1:4), and gave 2.3 g of 11 (39%). $^1$H NMR (200 MHz, CDCl$_3$): δ 1.24 (t, J=7.04 Hz, 6H), 3.40 (d, J=22.00 Hz, 2H), 4.03 (m, 4H), 6.91 (m, 1H), 7.32 (m, 1H), 7.44 (m, 1H), 7.82 (m, 1H); $^{13}$C NMR (50 MHz, CDCl$_3$): δ 16.27 (J=6.00 Hz), 38.31 (J=137.50 Hz), 62.16 (J=6.70 Hz), 101.16 (J=9.45 Hz), 128.23 (J=3.35 Hz), 128.45 (J=3.55 Hz), 130.60 (J=5.10 Hz), 135.36 (J=8.80 Hz), 139.60 (J=2.85 Hz).

EXAMPLE 2

(E)-2'-Iodo-N,N-dimethyl-4-stilbenamine (4)

To a mixture of NaH (2 mmol, 80% suspension in oil), and 3-iodobenzylphosphonate 2 (500 mg, 1.42 mmol) in 6 mL of THF at 80° C. under nitrogen atmosphere, was added dropwise 4-(dimethylamine)benzaldehyde (210 mg, 1.41 mmol). After overnight at room temperature, NH$_4$Cl solution (saturated, 5 mL) was added and the mixture was extracted with CH$_2$Cl$_2$ (3×30 mL). The combined organic extract was dried over Na$_2$SO$_4$ and evaporated to give (E)-2'-iodo-N,N-dimethyl-4-stilbenamine 11, which was purified by flash chromatography (EtOAc: Hex, 1:9) to give 3 (330 mg, 67%). $^1$H NMR (200 MHz, CDCl$_3$): δ 3.06 (s, 6H), 6.82 (m, 2H), 6.93-7.02 (m, 1H), 7.01 (d, J=15.98 Hz, 1H), 7.25 (d, J=15.99 Hz, 1H), 7.40 (m, 1H), 7.53-7.59 (m, 2H), 7.69 (dd, J=7.88 Hz, J=1.54 Hz, 1H), 7.95 (dd, J=7.92 Hz, J=1.20 Hz, 1H); $^{13}$C NMR (50 MHz, CDCl$_3$): δ 40.26, 100.20, 112.22, 125.12, 125.61, 127.83, 127.87, 127.97, 128.2, 131.66, 139.42, 140.84, 150.23; HRMS: m/z Calcd for C$_{16}$H$_{16}$IN, 349.0328; Found: 349.0342.

EXAMPLE 3

Diethyl 3-iodobenzylphosphonate (13)

A mixture of 3-iodobenzyl bromide 12 (5 g, 16.84 mmol) and triethyl phosphite (3.3 g, 20 mmol) was stirred at 160° C. After 4 h, the mixture was cooled to room temperature. The residue was subjected to flash chromatography (EtOAc: Hex, 1:4), and gave 5.4 g of 13 (91%). $^1$H NMR (200 MHz, CDCl$_3$): δ 1.15 (t, J=7.05 Hz, 6H), 2.97 (d, J=21.65 Hz, 2H), 3.92 (m, 4H), 6.93 (t, J=7.76 Hz, 1H), 7.17 (m, 1H), 7.52 (m, 2H); $^{13}$C NMR (50 MHz, CDCl$_3$): δ 16.25 (J=5.95 Hz), 33.15 (J=137.60 Hz), 62.19 (J=6.70 Hz), 94.13 (J=3.50 Hz), 128.89 (J=6.35 Hz), 130.07 (J=3.00 Hz), 133.95 (J=9.10 Hz), 135.87 (J=3.55 Hz), 138.51 (J=6.65 Hz).

EXAMPLE 4

(E)-3'-Iodo-N,N-dimethyl-4-stilbenamine (5)

To a mixture of NaH (2 mmol, 80% suspension in oil), and 3-iodobenzylphosphonate 13 (370 mg, 1.05 mmol) in 5 mL of THF at 80° C. under nitrogen atmosphere, was added dropwise 4-(dimethylamine)benzaldehyde (155 mg, 1.05 mmol). After overnight at room temperature, NH$_4$Cl solution (saturated, 5 mL) was added and the mixture was extracted with CH$_2$Cl$_2$ (3×20 mL). The combined organic extract was dried over Na$_2$SO$_4$ and evaporated to give (E)-3'-iodo-N,N-dimethyl-4-stilbenamine 5, which was purified by flash chromatography (EtOAc: Hex, 1:9) to give 3 (209 mg, 57%). $^1$H NMR (200 MHz, CDCl$_3$): δ 2.99 (s, 6H), 6.71 (m, 2H), 6.77 (d, J=16.41 Hz, 1H), 7.02 (d, J=16.22 Hz, 1H), 7.04 (t, J=7.8 Hz, 1H), 7.36-7.52 (m, 4H), 7.82 (s, 1H); $^{13}$C NMR (50 MHz, CDCl$_3$): δ 40.37, 94.78, 112.38, 112.53, 122.21, 127.76, 128.56, 130.19, 134.76, 135.34, 140.56, 150.36; HRMS: m/z Calcd for C$_{16}$H$_{16}$IN: 349.0328; Found: 349.0302.

EXAMPLE 5

Diethyl 4-iodobenzylphosphonate (15)

A mixture of 4-iodobenzyl bromide 14 (5.2 g, 17.51 mmol) and triethyl phosphite (3.3 g, 20 mmol) was stirred at 160° C. After 4 h, the mixture was cooled to room temperature. The residue was subjected to flash chromatography (EtOAc: Hex, 1:4), and gave 3.27 g of 15 (53%). $^1$H NMR (200 MHz, CDCl$_3$): δ1.24 (t, J=7.04 Hz, 6H), 3.07 (d, J=21.72 Hz, 2H), 4.01 (m, 4H), 7.04 (m, 2H), 7.62 (m, 2H); $^{13}$C NMR (50 MHz, CDCl$_3$): δ 16.24 (J=5.90 Hz), 33.21 (J=137.55 Hz), 62.04 (J=6.70 Hz), 92.15 (J=4.80 Hz), 131.31 (J=9.10 Hz), 131.57 (J=6.55 Hz), 137.43 (J=2.95 Hz).

EXAMPLE 6

(E)-4'-Iodo-N,N-dimethyl-4-stilbenamine (6)

To a mixture of NaH (2 mmol, 80% suspension in oil), and 4-iodobenzylphosphonate 15 (420 mg, 1.19 mmol) in 5 mL of THF at 80° C. under nitrogen atmosphere, was added dropwise 4-(dimethylamine)benzaldehyde (180 mg, 1.20 mmol). After overnight at room temperature, water (5 mL) was added. The solid formed was filtered and washed with ether to give crude 6 which was purified by recrystallization with CH$_2$Cl$_2$/hexane to afford pure 6 (156 mg, 38%). $^1$H NMR (200 MHz, CDCl$_3$): δ 2.99 (s, 6H), 6.71 (d, J=8.60 Hz, 2H), 6.81 (d, J=16.65 Hz, 1H), 7.04 (d, J=16.12 Hz, 1H), 7.21 (d, J=8.15 Hz, 1H), 7.38 (d, J=8.59 Hz, 2H), 7.63 (d, J=8.28 Hz, 2H); $^3$C NMR (50 MHz, CDCl$_3$): δ 40.39, 91.32, 112.38, 123.04, 127.69, 127.73, 128.23, 129.65, 137.55, 137.77, 150.29; HRMS: m/z Calcd for C$_{16}$H$_{16}$IN: 349.0328; Found: 349.0288.

EXAMPLE 7

(E)-4'-Iodo-4-O-methoxystilbenol (8)

To a mixture of NaH (2 mmol, 80% suspension in oil), and 3-iodobenzylphosphonate 13 (450 mg, 1.27 mmol) in 7 mL of THF at 80° C. under nitrogen atmosphere, was added dropwise p-anisaldehyde (172 mg, 1.27 mmol). After 3 days at room temperature, NH$_4$Cl solution (saturated, 5 mL) was added and the mixture was extracted with CH$_2$Cl$_2$ (3×30 mL). The combined organic extract was dried over Na$_2$SO$_4$, evaporated and purified by flash chromatography (EtOAc: Hex, 1:9) to give (E)-1-iodo-3-[2-(4-methoxyphenyl)ethenyl] benzene 8 (400 mg, 90%). $^1$H NMR (200 MHz, CDCl$_3$): δ 3.84 (s, 3H), 6.84 (d, J=16.29 Hz, 1H), 6.90 (m, 2H), 7.05 (d, J=16.30 Hz, 1H), 7.07 (t, J=7.8 Hz, 1H), 7.42-7.56 (m, 4H), 7.85 (s, 1H); $^{13}$C NMR (50 MHz, CDCl$_3$): δ 55.32, 94.76, 114.20, 124.85, 125.48, 127.88, 129.58, 129.62, 130.25, 135.00, 135.91, 139.97, 159.62; HRMS: m/z Calcd for C$_{15}$H$_{13}$IO: 336.0011; Found: 336.0006.

EXAMPLE 8

(E)-3'-Iodo-4-stilbenol (9)

To a solution of 8 (350 mg, 1.00 mmol) in CH$_2$Cl$_2$ (200 mL) was added BBr$_3$ (10 mL, 1M in hexane) dropwise at −78° C. in a dry ice-acetone bath. The mixture was allowed to warm up to room temperature. Water was added while the reaction mixture was cooled at 0° C. in an ice bath. The mixture was extracted with CH$_2$Cl$_2$. The organic phase was dried and filtered. The filtrate was purified by flash chromatography (EtOAc: Hex, 1:9) to give 9 (296 mg, 92%). $^1$H NMR (200 MHz, CDCl$_3$): δ 4.81 (s, 1H), 6.83 (d, J=16.17 Hz, 1H), 6.84 (m, 2H), 7.03 (d, J=16.32 Hz, 1H), 7.06 (t, J=7.8 Hz, 1H), 7.36-7.57 (m, 4H), 7.84 (s, 1H); $^{13}$C NMR (50 MHz, CDCl$_3$): δ 94.75, 115.67, 124.96, 125.49, 128.09, 129.48, 129.87, 130.25, 135.01, 135.96, 139.90, 155.53; HRMS: m/z Calcd for C$_{14}$H$_{11}$IO: 321.9855; Found: 321.9840.

EXAMPLE 9

Diethyl, 4-fluorobenzylphosphonate (17)

A mixture of 4-fluorobenzyl bromide 16 (1.89 g, 10 mmol) and triethyl phosphite (1.66 g, 10 mmol) was stirred at 170° C. for 4 h. The mixture was cooled to room temperature. and the residue was subjected to flash chromatography (EtOAc: Hex, 1:4) to gave 1.4 g of 17(57%).

$^1$H NMR (200 MHz, CDCl$_3$): δ 1.23 (t, J=7.1 Hz, 6H), 3.10 (d, J=21.4 Hz, 2H), 3.92 (q, J=7.1 Hz, 4H), 7.02 (m, 2H), 7.25 (m, 2H).

EXAMPLE 10

(E)-4-Fluoro-4'-dimethylamino-stilbene (7)

To a mixture of phosphate 17 (246 mg, 1 mmol) and 4-dimethylaminobenzaldehyde (149 mg, 1 mmol) in DMF (2 mL) was added KO$^t$Bu (224 mg, 2 mmol) in portions in solid form at RT. The resulting mixture was stirred at RT overnight. Water (10 mL) was added The solid was collected by suction and washed with water, dried to give 190 mg of product (80%).

$^1$H NMR (200 MHz, CDCl$_3$): δ 2.99 (s, 6H), 6.71 (d, J=8.9 Hz, 2H), 6.85 (d, J=16.3 Hz, 1H), 7.01 (t, J=8.7 Hz, 2H), 7.40 (d, J=9.0 Hz, 2H), 7.43 (m, 2H); $^3$C NMR (200 MHz, CDCl$_3$): δ 41.00, 113.01, 115.78, 116.21, 123.76, 126.18, 127.83, 127.99, 128.05, 129.19, 134.91, 150.72, 164.81.

EXAMPLE 11

(E)-3-Tributylstannyl-4'-dimethylamino-stilbene (18)

A mixture of 5 (139 mg, 0.38 mmol), bis-(tributytltin) (0.4 mL) and Pd(Ph$_3$P)$_4$ (30 mg) in a mixed solvent (20 mL, dioxane:triethylamine, 3:1) was stirred at 90° C. overnight. Solvent was removed and the residue was purified by PTLC (Hex:EtOAc, 2:1) to give 35 mg of product (18%, not optimized yield). $^1$H NMR (200 MHz, CDCl$_3$): δ 0.94 (t, J=7.2 Hz, 9H), 1.08-1.66 (m, 18H), 3.01 (s, 6H), 6.75 (m, 2H), 6.94 (d, J=16.3 Hz, 1H), 7.08 (d, J=16.3 Hz, 1H), 7.25-7.57 (m, 6H); $^{13}$C NMR (50 MHz, CDCl$_3$): δ 9.56, 13.67, 27.37, 29.10, 40.45, 112.45, 124.84, 125.44, 125.98, 127.51, 128.01, 128.51, 134.36, 134.89, 137.41, 142.09, 150.06; HRMS: m/z Calcd for C$_{28}$H$_{44}$NSn (MH$^+$): 514.2496; Found: 514.2512.

EXAMPLE 12

Preparation of Radioiodinated Ligand

The desired $^{125}$I-labeled compound was prepared using iododestannylation reactions with tributyltin precursor of 5. Hydrogen peroxide (50 μL, 3% w/v) was added to a mixture of 50 μL of the corresponding tributyltin precursor, 18, (1 μg/μL EtOH), 50 μL of 1N HCl and [$^{125}$I]NaI (1-5 mCi) in a closed vial. The reaction was allowed to proceed for 10 min at room temperature and terminated by addition of 100 μL of sat. NaHSO$_3$. The reaction mixture was extracted with ethyl acetate (3×1 mL) after neutralization with saturated sodium bicarbonate solution. The combined extracts were evaporated to dryness. The residue was dissolved in 100 μL of EtOH and purified by HPLC using a reversed phase column (Waters C-18 ubondpad, 3.9×300 mm) with an isocratic solvent of 80% acetonitrile-20% of buffer, 3,3-dimethylglutaric acid (5 mM, pH 7.0) in a flow rate of 0.8 mL/min. The desired fractions containing the product were collected, condensed and re-extracted with ethyl acetate. The no-carrier-added product was evaporated to dryness and re-dissolved in 100% EtOH (1 μCi/μL), The final $^{125}$I probe, with a specific activity of 2,200 Ci/mmole and a greater than 95% radiochemical purity, was stored at −20° C. up to 6 weeks for in vitro binding studies.

EXAMPLE 13

Binding Assays Using Aggregated Aβ(1-40) Peptide in Solution

Figure 2:
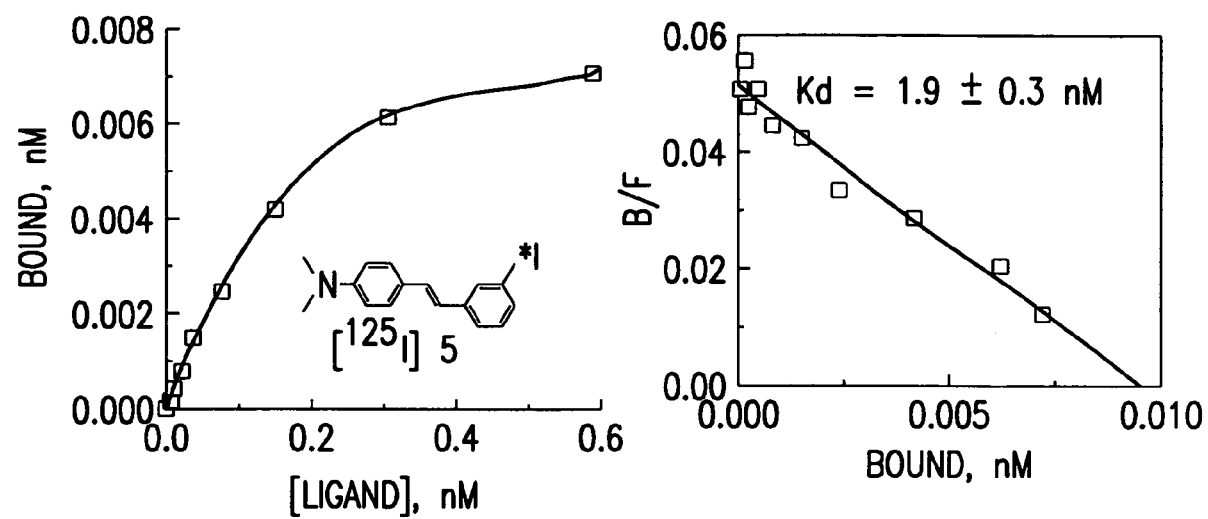
FIG. 2 depicts the binding data for a compound of the present invention.
Figure 3:
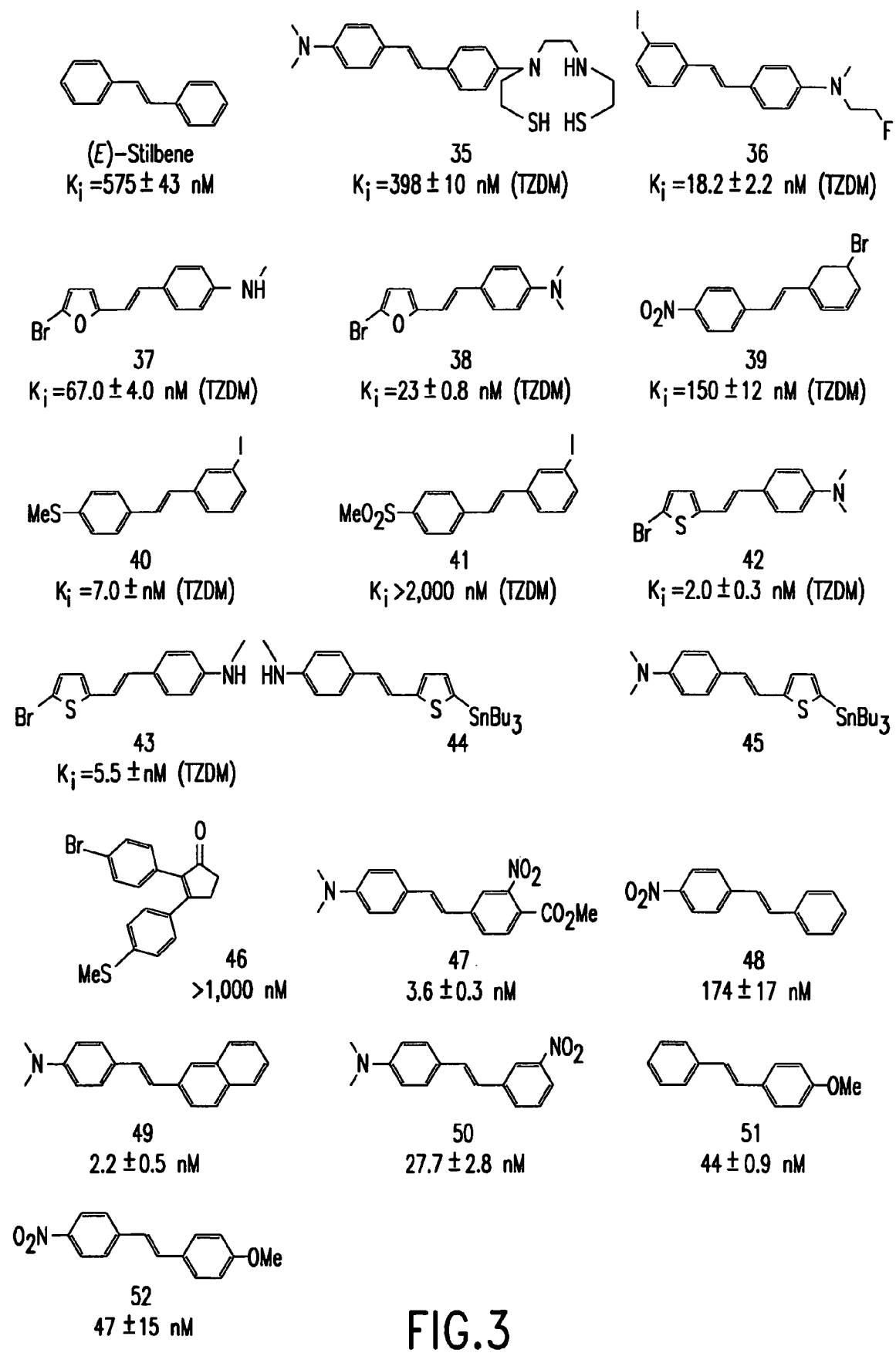
Figure 4:
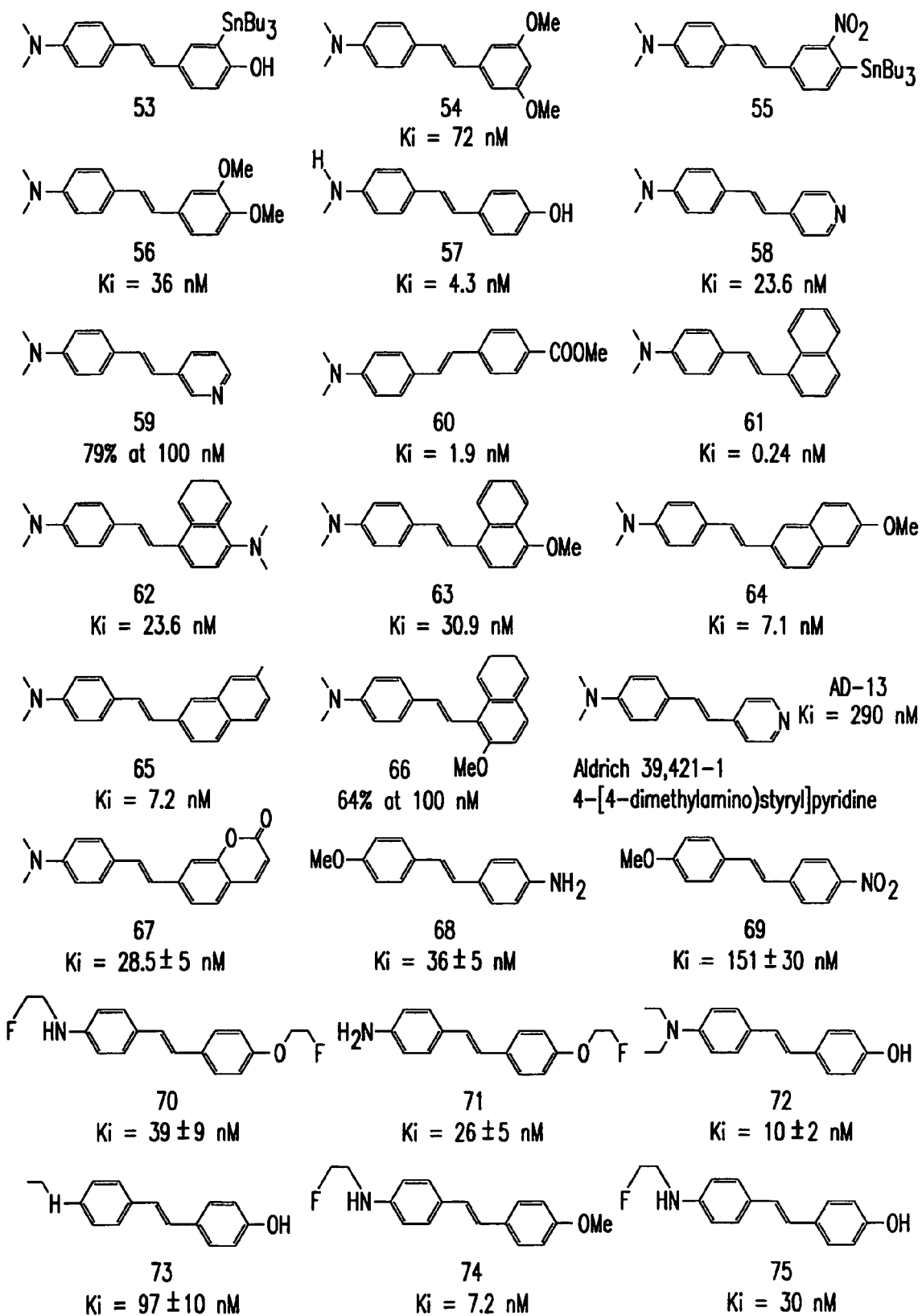
Figure 5:
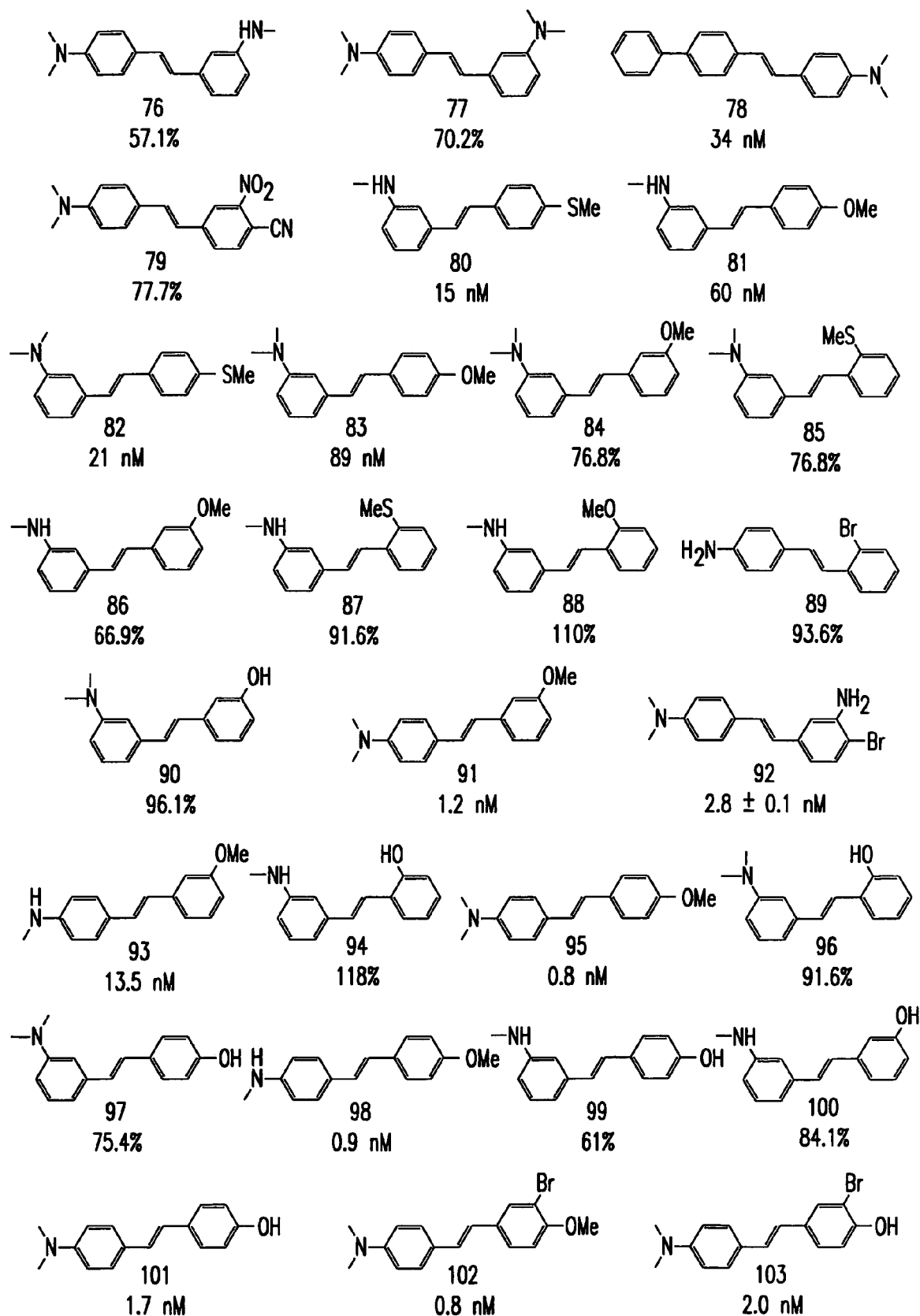

The solid forms of peptides Aβ(1-40) was purchased from Bachem (King of Prussia, Pa.). Peptide aggregation was carried out by gently dissolving the peptide (0.5 mg/mL) in a buffer solution (pH 7.4) containing 10 mM sodium phosphate and 1 mM EDTA. The solution was incubated at 37° C. for 36-42 h with gentle and constant shaking. Binding studies were carried out in 12×75 mm borosilicate glass tubes according to the procedure described[1]. Aggregated fibrils (10-50 nM in the final assay mixture) were added to the mixture containing 50 μl of radioligands (0.01-0.5 nM in 40% EtOH) and 10% EtOH in a final volume of 1 mL for saturation studies. The final concentration of EtOH was 10%. Nonspecific binding was defined in the presence of 2 μM thioflavin T. For inhibition studies, 1 mL of the reaction mixture contained 40 μl of inhibitors (10$^{-5}$-10$^{-10}$ M in 10% EtOH) and 0.05 nM radiotracer in 40% EtOH. The mixture was incubated at room temperature for 3 h and the bound and the free radioactivities were separated by vacuum filtration through Whatman GF/B filters using a Brandel M-24R cell harvester followed by 2×3 mL washes of 10% ethanol at room temperature. Filters containing the bound I-125 ligand were counted in a gamma counter (Packard 5000) with 70% counting efficiency. Under the assay conditions, the percent of the specifically bound fraction was less than 20% of the total radioactivity. The results of saturation and inhibition experiments were subjected to nonlinear regression analysis using software EBDA$^2$ by which $K_d$ and $K_i$ values were calculated. Values for ($K_i$, nM) are the mean±SEM of three independent experiments, each in duplicate. Additional $K_i$ values for compounds of Formula I are provided in FIGS. 1 and 2.

In in vitro binding assays using pre-formed Aβ aggregates of synthetic peptides and [$^{125}$I]TZDM as the ligand, these novel stilbenes showed exceedingly high binding affinity (2-40 nM) to the TZ sites, while the affinity towards SB sites was very low (>1,000 nM). It is evident that the stilbenes containing an electron donating groups, such as dimethylamino-, —OH or —OMe group, showed excellent binding affinity to Aβ aggregates. Benzothiazole ring appears to be unnecessary for binding at the TZ binding sites of Aβ aggregates. This information is of paramount importance because it reduces the molecular size (molecular weight of TZDM and 1 was 380 and 349, respectively) required for binding to the TZ sites; as such it significantly enhances the flexibility on designing new ligands. The idoinated stilbenes, such as 2 and 5, respresent a structural simplicity, which suggests minimum requirements for binding the Aβ aggregates may be three: 1) two benzene rings separated by a vinyl group. 2) one of the aromatic ring contains a electronic negative group, dimethylamino-, —OH or —OMe group. 3) there appears to be a bulk tolerance for substitution on the second aromatic ring. To characterize the compounds further, radioactive iodinated ligand, [$^{125}$I]2, was prepared by converting the corresponding tributyltin derivative in the presence of Na[$^{125}$I]I and hydrogen peroxide, by which the no-carrier added product was obtained in excellent yield (radiochemical purity>95%). The direct binding assay showed that the new evaluation of postmortem AD brain sections with [$^{125}$I]2 suggested that the novel ligand, as expected, labeled Aβ plaques.

EXAMPLE 14

In Vivo Biodistribution of New Probes in Normal Mice

While under ether anesthesia, 0.15 mL of a saline solution containing the labeled agent (5-10 μCi) was injected directly into the tail vein of ICR mice (2-3 month-old, average weight 20-30 g). The mice were sacrificed by cardiac excision at various time points post injection. The organs of interest were removed and weighed, and the radioactivity was counted with an automatic gamma counter (Packard 5000). The percentage dose per organ was calculated by a comparison of the tissue counts to suitably diluted aliquots of the injected material. Total activities of blood and muscle were calculated under the assumption that they were 7% and 40% of the total body weight, respectively.

In vivo biodistribution study of [$^{125}$I]2 in normal mice after an iv injection suggested good brain penetration. The brain uptake was 0.84, 1.08, 0.91, and 0.54% dose/organ, at 2, 30, 60 and 120 minutes after injection (the blood levels was relatively low 5.2-3.6% dose/organ at all of the time points). Radioactive ligand's binding to the aggregates of Aβ$_{1-40}$ is saturable and the $K_d$ was 0.2 nM.

Having now fully described this invention, it will be understood to those of ordinary skill in the art that the same can be performed within a wide and equivalent range of conditions, formulations, and other parameters without affecting the scope of the invention or any embodiment thereof. All patents, patent applications, and publications cited herein are fully incorporated by reference herein in their entirety.

What is claimed is:

1. A compound of general Formula III:

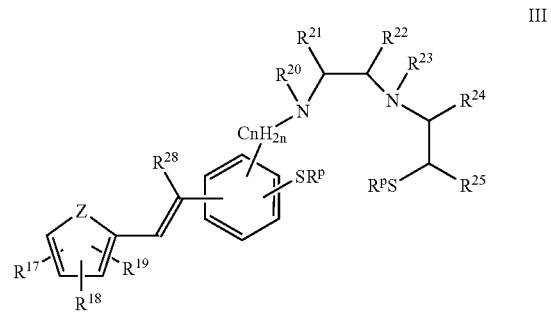

or a pharmaceutically acceptable salt thereof, wherein:
$R^{28}$ is hydrogen or $C_{1-4}$ alkyl,
n is equal to a number from zero to four,
Z is —CR$^{15}$=CR$^{16}$—, wherein
$R^{15}$, $R^{16}$, $R^{17}$, $R^{18}$, $R^{19}$, $R^{20}$, $R^{21}$, $R^{22}$, $R^{23}$, $R^{24}$ and $R^{25}$ are independently selected from the group consisting of:
  a. hydrogen
  b. $C_{1-4}$ alkylthio,
  c. hydroxy,
  d. $C_{1-4}$ alkoxy,
  e. NR$^{26}$R$^{27}$, wherein
    $R^{26}$ and $R^{27}$ are hydrogen or $C_{1-4}$ alkyl,
  f. phenyl($C_{1-4}$)alkyl,
  g. $C_{6-10}$ aryl,
  h. heteroaryl,
  i. heterocycle,
  j. heterocycle($C_{1-4}$)alkyl, and
  k. $C_{3-6}$ cycloalkyl,
    wherein said phenyl($C_{1-4}$)alkyl, $C_{6-10}$ aryl, heteroaryl, heterocycle, heterocycle($C_{1-4}$)alkyl or $C_{3-6}$ cycloalkyl is substituted with one of the following: $C_{1-4}$ alkylthio, $C_{1-4}$ alkyl, methoxy, hydroxy, dimethylamino or methylamino;
provided that one or more of $R^{15}$, $R^{16}$, $R^{17}$, $R^{18}$, $R^{19}$, $R^{20}$, $R^{21}$, $R^{22}$, $R^{23}$, $R^{24}$ and $R^{25}$ is other than hydrogen; and,
$R^P$ is hydrogen or a sulfur protecting group.

2. A compound of claim 1, wherein
$R^{17}$ is NR$^{26}$R$^{27}$ wherein
  $R^{26}$ and $R^{27}$ are as described above, and
$R^{15}$, $R^{16}$, $R^{18}$, $R^{19}$, $R^{20}$, $R^{21}$, $R^{22}$, $R^{23}$, $R^{24}$, $R^{25}$ and $R^{28}$ are hydrogen.

3. A compound of claim 1, wherein n is equal to zero.

4. A compound of claim 1, wherein $R^{26}$ and $R^{27}$ are independently hydrogen or $C_{1-4}$ alkyl.

5. A compound of claim 4, wherein $R^{26}$ and $R^{27}$ are methyl.

6. A compound of general Formula V:

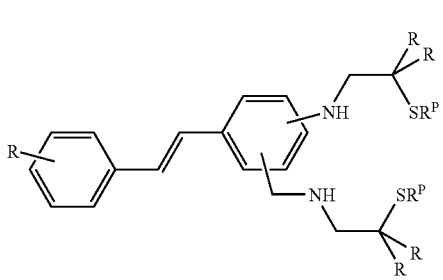

or a pharmaceutically acceptable salt thereof, wherein:
R is, in each instance, independently selected from the group consisting of:
  a. $C_{1-4}$ alkylthio,
  b. halo($C_{1-4}$)alkoxy,
  c. carboxy($C_{1-5}$)alkyl,
  d. hydroxy,
  e. $C_{1-4}$ alkoxy,
  f. $NR^{36}R^{37}$, wherein
    $R^{36}$ and $R^{37}$ are hydrogen, fluoro($C_{1-4}$)alkyl or $C_{1-4}$ alkyl,
  g. phenyl($C_{1-4}$)alkyl,
  h. $C_{6-10}$ aryl,
  i. heteroaryl,
  j. heterocycle,
  k. heterocycle($C_{1-4}$)alkyl,
  l. $C_{3-6}$ cycloalkyl,
    wherein said phenyl($C_{1-4}$)alkyl, $C_{6-10}$ aryl, heteroaryl, heterocycle, heterocycle($C_{1-4}$)alkyl or $C_{3-6}$ cycloalkyl is substituted with one of the following: $C_{1-4}$ alkylthio, $C_{1-4}$ alkyl sulfonyl, methoxy, hydroxy, dimethylamino or methylamino, and
  m. alkyl; and
$R^P$ is hydrogen or a sulfur protecting group.

7. A compound of claim 6, wherein said protecting group is selected from the group consisting of methoxymethyl, methoxyethoxymethyl, p-methoxybenzyl or benzyl.

8. A pharmaceutical composition comprising a compound of claim 1.

9. A compound having the following structure:

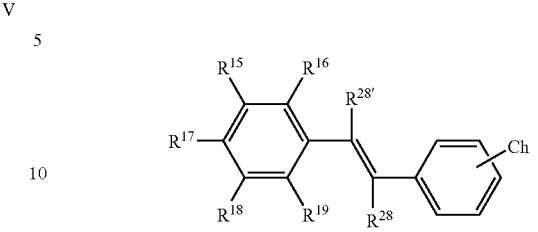

or a pharmaceutically acceptable salt thereof, wherein:
$R^{28}$ and $R^{28'}$ are each independently hydrogen or $C_{1-4}$ alkyl, —Ch is a $N_2S_2$-type metal chelating moiety,
$R^{15}$, $R^{16}$, $R^{17}$, $R^{18}$, $R^{19}$, $R^{20}$, $R^{21}$, $R^{22}$, $R^{23}$, $R^{24}$ and $R^{25}$ are independently selected from the group consisting of:
  a. hydrogen
  b. $C_{1-4}$ alkylthio,
  C. hydroxy,
  d. $C_{1-4}$ alkoxy,
  e. $NR^{26}R^{27}$, wherein
    $R^{26}$ and $R^{27}$ are hydrogen or $C_{1-4}$ alkyl,
  f. phenyl($C_{1-4}$)alkyl,
  g. $C_{6-10}$ aryl,
  h. heteroaryl,
  i. heterocycle,
  j. heterocycle($C_{1-4}$)alkyl, and
  k. $C_{3-6}$ cycloalkyl,
    wherein said phenyl($C_{1-4}$)alkyl, $C_{6-10}$ aryl, heteroaryl, heterocycle, heterocycle($C_{1-4}$)alkyl or $C_{3-6}$ cycloalkyl is substituted with one of the following: $C_{1-4}$ alkylthio, $C_{1-4}$ alkyl, methoxy, hydroxy, dimethylamino or methylamino;
provided that one or more of $R^{15}$, $R^{16}$, $R^{17}$, $R^{18}$, $R^{19}$, $R^{20}$, $R^{21}$, $R^{22}$, $R^{23}$, $R^{24}$ and $R^{25}$ is other than hydrogen.

10. The compound of claim 9, one or more of $R^{15}$, $R^{16}$, $R^{18}$, $R^{19}$, $R^{20}$, $R^{21}$, and $R^{17}$ is hydroxy or $NR^{26}R^{27}$, wherein $R^{26}$ and $R^{27}$ are hydrogen or $C_{1-4}$ alkyl.

* * * * *